(12) United States Patent
Fiser et al.

(10) Patent No.: US 7,361,159 B2
(45) Date of Patent: Apr. 22, 2008

(54) PASSIVE SAFETY SHIELD

(75) Inventors: Richard L. Fiser, Kirkwood, MO (US); Alan B. Ranford, St. Louis County, MO (US); James L. Carlyon, Leadwood, MO (US); Eugene Weilbacher, Chesterfield, MO (US); Lee Burnes, Wilbraham, MA (US)

(73) Assignee: Covidien AG (CH)

( * ) Notice: Subject to any disclaimer, the term of this patent is extended or adjusted under 35 U.S.C. 154(b) by 730 days.

(21) Appl. No.: 10/275,209

(22) PCT Filed: Mar. 4, 2002

(86) PCT No.: PCT/US02/06524

§ 371 (c)(1),
(2), (4) Date: Feb. 4, 2003

(87) PCT Pub. No.: WO02/070056

PCT Pub. Date: Sep. 12, 2002

(65) Prior Publication Data

US 2004/0044318 A1   Mar. 4, 2004

Related U.S. Application Data

(60) Provisional application No. 60/272,864, filed on Mar. 2, 2001.

(51) Int. Cl.
*A61M 5/32* (2006.01)
(52) U.S. Cl. .................................... 604/192
(58) Field of Classification Search ............... 604/192, 604/198, 263, 187, 110
See application file for complete search history.

(56) References Cited

U.S. PATENT DOCUMENTS

| | | | |
|---|---|---|---|
| 1,779,451 A | 10/1930 | Sponsel | |
| 2,559,474 A | 7/1951 | Son | 128/215 |
| 2,700,385 A | 1/1955 | Ortiz | 128/215 |
| 2,836,942 A | 6/1958 | Miskel | 53/25 |
| 2,854,976 A | 10/1958 | Heydrich | 128/221 |
| 2,953,243 A | 9/1960 | Roehr | 206/43 |
| 3,021,942 A | 2/1962 | Hamilton | 206/43 |
| 3,073,307 A | 1/1963 | Stevens | 128/221 |
| 3,074,542 A | 1/1963 | Myerson et al. | 206/43 |
| 3,255,873 A | 6/1966 | Speelman | 206/56 |
| 3,294,231 A | 12/1966 | Vanderbeck | 206/63 |

(Continued)

FOREIGN PATENT DOCUMENTS

EP   0 144 483 A2   6/1985

(Continued)

*Primary Examiner*—Manuel Mendez

(57) ABSTRACT

A safety apparatus is provided which includes a needle hub having an arm extending therefrom and an extensible frame connected to the needle hub. The extensible frame includes a proximal segment that is hingedly connected to a distal segment. The extensible frame is resiliently biased from a retracted position to an extended position, wherein the arm releasably enages the promixmal segment to fix the extensible frame in a position between the retracted position and the extended position. In an alternate embodiment, the safety apparatus includes an extensible frame including a proximal segment which is hingedly connected to a distal segment. A resilient member is coupled to the proximal segment and the distal segment. The resilient member is configured to bias the extensible frame from a retracted position to an extended position. A method for infusing fluids to a subject is disclosed.

16 Claims, 16 Drawing Sheets

U.S. PATENT DOCUMENTS

| | | | | |
|---|---|---|---|---|
| 3,323,523 A | 6/1967 | Scislowicz et al. | ......... | 128/214 |
| 3,329,146 A | 7/1967 | Waldman, Jr. | ............... | 128/221 |
| 3,333,682 A | 8/1967 | Burke | .......................... | 206/43 |
| 3,367,488 A | 2/1968 | Hamilton | ................... | 206/63 |
| 3,485,239 A | 12/1969 | Vanderbeck | ............... | 128/218 |
| 3,537,452 A | 11/1970 | Wilks | ........................ | 128/214 |
| 3,587,575 A | 6/1971 | Lichtenstein | ............... | 128/215 |
| 3,610,240 A | 10/1971 | Harautuneian | .............. | 128/214 |
| 3,645,835 A | 2/1972 | Hodgson | .................. | 428/195.1 |
| 3,658,061 A | 4/1972 | Hall | ............................ | 128/214 |
| 3,828,775 A | 8/1974 | Armel | ........................ | 128/218 |
| 3,840,008 A | 10/1974 | Noiles | ........................ | 128/221 |
| 3,890,971 A | 6/1975 | Leeson et al. | ................ | 128/214 |
| 3,904,033 A | 9/1975 | Haerr | ........................ | 206/349 |
| 3,918,446 A | 11/1975 | Buttaravoli | ................ | 604/180 |
| 3,934,722 A | 1/1976 | Goldberg | ................... | 206/365 |
| 3,968,876 A | 7/1976 | Brookfield | ................. | 206/365 |
| 4,040,419 A | 8/1977 | Goldman | .................. | 128/215 |
| 4,106,621 A | 8/1978 | Sorenson | .................. | 206/365 |
| 4,113,090 A | 9/1978 | Carstens | .................... | 206/365 |
| 4,139,009 A | 2/1979 | Alvarez | ..................... | 128/218 |
| 4,175,008 A | 11/1979 | White | ........................ | 435/295 |
| 4,270,536 A | 6/1981 | Lemelson | ................... | 128/218 |
| 4,300,678 A | 11/1981 | Gyure et al. | ................ | 206/364 |
| 4,375,849 A | 3/1983 | Hanifl | ........................ | 206/366 |
| 4,430,082 A | 2/1984 | Schwabacher | .............. | 604/263 |
| 4,592,744 A | 6/1986 | Jagger et al. | ................ | 604/192 |
| 4,634,428 A | 1/1987 | Cuu | ............................ | 604/110 |
| 4,643,722 A | 2/1987 | Smith, Jr. | ................... | 604/192 |
| 4,659,330 A | 4/1987 | Nelson et al. | ............... | 604/192 |
| 4,664,259 A | 5/1987 | Landis | ........................ | 206/365 |
| 4,664,654 A | 5/1987 | Strauss | ....................... | 604/198 |
| 4,681,567 A | 7/1987 | Masters et al. | .............. | 604/198 |
| 4,695,274 A | 9/1987 | Fox | ............................ | 604/198 |
| 4,702,738 A | 10/1987 | Spencer | ..................... | 604/198 |
| 4,723,943 A | 2/1988 | Spencer | ..................... | 604/198 |
| 4,728,320 A | 3/1988 | Chen | .......................... | 604/110 |
| 4,728,321 A | 3/1988 | Chen | .......................... | 604/110 |
| 4,731,059 A | 3/1988 | Wanderer et al. | ........... | 604/192 |
| 4,735,311 A | 4/1988 | Lowe et al. | ................. | 206/365 |
| 4,735,618 A | 4/1988 | Hagen | ........................ | 604/192 |
| 4,737,144 A | 4/1988 | Choksi | ....................... | 604/198 |
| 4,738,663 A | 4/1988 | Bogan | ........................ | 604/198 |
| 4,743,233 A | 5/1988 | Schneider | .................. | 604/192 |
| 4,747,836 A | 5/1988 | Luther | ........................ | 604/198 |
| 4,747,837 A | 5/1988 | Hauck | ........................ | 604/198 |
| 4,772,272 A | 9/1988 | McFarland | .................. | 604/198 |
| 4,778,453 A | 10/1988 | Lopez | ........................ | 604/110 |
| 4,781,697 A | 11/1988 | Slaughter | ................... | 604/192 |
| 4,782,841 A | 11/1988 | Lopez | ........................ | 128/164 |
| 4,790,828 A | 12/1988 | Dombrowski et al. | ...... | 604/198 |
| 4,795,432 A | 1/1989 | Karczmer | ................... | 604/110 |
| 4,795,443 A | 1/1989 | Permenter et al. | .......... | 604/198 |
| 4,801,295 A | 1/1989 | Spencer | ..................... | 604/198 |
| 4,804,372 A | 2/1989 | Laico et al. | ................. | 604/192 |
| 4,813,426 A | 3/1989 | Haber et al. | ................ | 128/763 |
| 4,816,022 A | 3/1989 | Poncy | ........................ | 604/198 |
| 4,816,024 A | 3/1989 | Sitar et al. | ................... | 604/192 |
| 4,819,659 A | 4/1989 | Sitar | .......................... | 128/764 |
| 4,820,277 A | 4/1989 | Norelli | ....................... | 604/192 |
| 4,826,490 A | 5/1989 | Byrne et al. | ................. | 604/198 |
| 4,826,491 A | 5/1989 | Schramm | ................... | 604/198 |
| 4,838,871 A | 6/1989 | Luther | ........................ | 604/192 |
| 4,840,619 A | 6/1989 | Hughes | ...................... | 604/187 |
| 4,842,587 A | 6/1989 | Poncy | ........................ | 604/198 |
| 4,846,796 A | 7/1989 | Carrell et al. | ............... | 604/110 |
| 4,846,811 A | 7/1989 | Vanderhoof | ................. | 604/263 |
| 4,850,968 A | 7/1989 | Romano | .................... | 604/110 |
| 4,850,976 A | 7/1989 | Heinrich et al. | ............. | 604/192 |
| 4,850,977 A | 7/1989 | Bayless | ..................... | 604/198 |
| 4,850,978 A | 7/1989 | Dudar et al. | ................ | 604/201 |
| 4,850,994 A | 7/1989 | Zerbst et al. | ............... | 604/198 |
| 4,850,996 A | 7/1989 | Cree | .......................... | 604/198 |
| 4,858,607 A | 8/1989 | Jordan et al. | ............... | 128/314 |
| 4,863,434 A | 9/1989 | Bayless | ..................... | 604/198 |
| 4,863,435 A | 9/1989 | Sturman et al. | ............. | 604/198 |
| 4,863,436 A | 9/1989 | Glick | ......................... | 604/198 |
| 4,867,172 A | 9/1989 | Haber et al. | ................ | 128/763 |
| 4,867,746 A | 9/1989 | Dufresne | .................... | 604/192 |
| 4,872,552 A | 10/1989 | Unger | ........................ | 206/365 |
| 4,874,382 A | 10/1989 | Lindemann et al. | ......... | 604/195 |
| 4,874,383 A | 10/1989 | McNaughton | .............. | 604/198 |
| 4,874,384 A | 10/1989 | Nunez | ........................ | 604/198 |
| 4,883,469 A | 11/1989 | Glazier | ....................... | 604/192 |
| 4,886,503 A | 12/1989 | Miller | ......................... | 604/192 |
| 4,887,998 A | 12/1989 | Martin et al. | ............... | 604/110 |
| 4,888,001 A | 12/1989 | Schoenberg | ................ | 604/162 |
| 4,892,107 A | 1/1990 | Haber | ........................ | 128/763 |
| 4,892,521 A | 1/1990 | Laico et al. | ................. | 604/192 |
| 4,898,589 A | 2/1990 | Dolgin et al. | ............... | 604/198 |
| 4,900,309 A | 2/1990 | Netherton et al. | .......... | 604/192 |
| 4,904,244 A | 2/1990 | Harsh et al. | ................ | 604/187 |
| 4,911,694 A | 3/1990 | Dolan | ........................ | 604/198 |
| 4,911,706 A | 3/1990 | Levitt | ......................... | 604/198 |
| 4,927,018 A | 5/1990 | Yang et al. | ................. | 206/365 |
| 4,929,241 A | 5/1990 | Kulli | .......................... | 604/263 |
| 4,935,012 A | 6/1990 | Magre et al. | ............... | 604/192 |
| 4,935,013 A | 6/1990 | Haber et al. | ................ | 604/192 |
| 4,936,830 A | 6/1990 | Verlier | ........................ | 604/110 |
| 4,944,397 A | 7/1990 | Miller | ......................... | 206/365 |
| 4,944,731 A | 7/1990 | Cole | .......................... | 604/192 |
| 4,950,249 A | 8/1990 | Jagger et al. | ................ | 604/192 |
| 4,950,250 A | 8/1990 | Haber et al. | ................ | 604/192 |
| 4,966,589 A | 10/1990 | Kaufman | .................... | 604/174 |
| 4,978,344 A | 12/1990 | Dombrowski et al. | ...... | 604/198 |
| 4,982,842 A | 1/1991 | Hollister | ..................... | 206/365 |
| 4,985,021 A | 1/1991 | Straw et al. | ................. | 604/198 |
| 4,994,041 A | 2/1991 | Dombrowski et al. | ...... | 604/164 |
| 5,000,744 A | 3/1991 | Hoffman et al. | ............ | 604/232 |
| 5,015,240 A | 5/1991 | Soproni et al. | .............. | 604/192 |
| 5,057,089 A | 10/1991 | Greco | ........................ | 604/198 |
| 5,059,180 A | 10/1991 | McLees | ...................... | 604/110 |
| 5,092,851 A | 3/1992 | Ragner | ....................... | 604/192 |
| 5,108,379 A | 4/1992 | Dolgin et al. | ............... | 604/198 |
| RE34,045 E | 8/1992 | McFarland | .................. | 604/198 |
| 5,135,509 A | 8/1992 | Olliffee | ....................... | 604/192 |
| 5,139,489 A | 8/1992 | Hollister | ..................... | 604/192 |
| 5,147,303 A | 9/1992 | Martin | ........................ | 604/110 |
| 5,154,285 A | 10/1992 | Hollister | ..................... | 206/365 |
| 5,176,655 A | 1/1993 | McCormick et al. | ........ | 604/198 |
| 5,176,656 A | 1/1993 | Bayless | ..................... | 604/198 |
| 5,193,552 A | 3/1993 | Columbus et al. | .......... | 128/760 |
| 5,195,983 A | 3/1993 | Boese | ........................ | 604/192 |
| 5,209,739 A | 5/1993 | Talalay | ....................... | 604/195 |
| 5,232,454 A | 8/1993 | Hollister | ..................... | 604/192 |
| 5,232,455 A | 8/1993 | Hollister | ..................... | 604/192 |
| 5,242,417 A * | 9/1993 | Paudler | ....................... | 604/192 |
| 5,242,418 A | 9/1993 | Weinstein | ................... | 604/192 |
| 5,246,427 A | 9/1993 | Sturman et al. | ............. | 604/192 |
| 5,246,428 A | 9/1993 | Falknor | ....................... | 604/198 |
| 5,250,031 A | 10/1993 | Kaplan et al. | ............... | 604/110 |
| 5,254,099 A | 10/1993 | Kuracina et al. | ............ | 604/198 |
| 5,256,152 A | 10/1993 | Marks | ........................ | 604/198 |
| 5,256,153 A | 10/1993 | Hake | .......................... | 604/198 |
| 5,277,311 A | 1/1994 | Hollister | ..................... | 206/365 |
| 5,290,255 A | 3/1994 | Vallelunga et al. | ......... | 604/197 |
| 5,304,137 A | 4/1994 | Fluke | ......................... | 604/110 |
| 5,312,369 A | 5/1994 | Arcusin et al. | .............. | 604/192 |
| 5,334,158 A | 8/1994 | McLees | ...................... | 604/110 |
| 5,348,544 A * | 9/1994 | Sweeney et al. | ............. | 604/192 |
| 5,356,392 A | 10/1994 | Firth et al. | .................. | 604/198 |
| 5,372,589 A | 12/1994 | Davis | ........................ | 604/180 |
| 5,403,283 A | 4/1995 | Luther | ........................ | 604/164 |
| 5,403,286 A | 4/1995 | Lockwood, Jr. | ............ | 604/110 |

| Patent No. | Date | Name | Class |
|---|---|---|---|
| 5,407,436 A | 4/1995 | Toft et al. | 604/195 |
| 5,411,492 A | 5/1995 | Sturman et al. | 604/263 |
| 5,423,765 A | 6/1995 | Hollister | 604/192 |
| 5,423,766 A | 6/1995 | Di Cesare | 604/192 |
| 5,425,720 A | 6/1995 | Rogalsky et al. | 604/198 |
| 5,445,618 A | 8/1995 | Adobbati | 604/192 |
| 5,447,501 A | 9/1995 | Karlsson et al. | 604/198 |
| 5,466,223 A | 11/1995 | Bressler et al. | 604/110 |
| 5,480,385 A | 1/1996 | Thorne et al. | 604/110 |
| 5,487,733 A | 1/1996 | Caizza et al. | 604/110 |
| 5,487,734 A | 1/1996 | Thorne et al. | 604/195 |
| 5,490,841 A | 2/1996 | Landis | 604/110 |
| 5,498,243 A | 3/1996 | Vallelunga et al. | 604/197 |
| 5,531,694 A | 7/1996 | Clemens et al. | 604/110 |
| 5,533,980 A | 7/1996 | Sweeney et al. | 604/192 |
| 5,536,240 A | 7/1996 | Edwards et al. | 604/22 |
| 5,538,508 A | 7/1996 | Steyn | 604/192 |
| 5,542,927 A | 8/1996 | Thorne et al. | 604/110 |
| 5,549,568 A | 8/1996 | Shields | 604/192 |
| 5,549,570 A | 8/1996 | Rogalsky | 604/198 |
| 5,549,708 A | 8/1996 | Thorne et al. | 604/110 |
| 5,562,629 A | 10/1996 | Haughton et al. | 604/158 |
| 5,562,631 A | 10/1996 | Bogert | 604/164 |
| 5,573,510 A | 11/1996 | Isaacson | 604/158 |
| 5,584,816 A | 12/1996 | Gyure et al. | 604/192 |
| 5,584,818 A | 12/1996 | Morrison | 604/197 |
| 5,599,318 A | 2/1997 | Sweeney et al. | 604/263 |
| 5,611,782 A | 3/1997 | Haedt | 604/198 |
| 5,643,220 A | 7/1997 | Cosme | 604/192 |
| 5,672,161 A | 9/1997 | Allen et al. | 604/263 |
| 5,695,474 A | 12/1997 | Daugherty | 604/162 |
| 5,695,477 A | 12/1997 | Sfikas | 604/241 |
| 5,700,249 A | 12/1997 | Jenkins | 604/263 |
| 5,735,827 A | 4/1998 | Adwers et al. | 604/263 |
| 5,738,665 A | 4/1998 | Caizza et al. | 604/263 |
| 5,746,718 A | 5/1998 | Steyn | 604/192 |
| 5,746,726 A | 5/1998 | Sweeney et al. | 604/263 |
| 5,755,699 A | 5/1998 | Blecher et al. | 604/198 |
| 5,814,018 A | 9/1998 | Elson et al. | 604/110 |
| 5,817,064 A | 10/1998 | DeMarco et al. | 604/198 |
| 5,823,997 A | 10/1998 | Thorne | 604/110 |
| 5,843,041 A | 12/1998 | Hake et al. | 604/198 |
| 5,879,330 A | 3/1999 | Bell | 604/93 |
| 5,885,249 A * | 3/1999 | Irisawa | 604/111 |
| 5,910,130 A * | 6/1999 | Caizza et al. | 604/110 |
| 5,919,168 A | 7/1999 | Wheeler | 604/198 |
| 5,921,969 A | 7/1999 | Vallelunga et al. | 604/263 |
| 5,925,020 A | 7/1999 | Nestell | 604/198 |
| 5,951,522 A | 9/1999 | Rosato et al. | 604/177 |
| 5,957,892 A | 9/1999 | Thorne | 604/162 |
| 5,980,488 A | 11/1999 | Thorne | 604/110 |
| 5,997,504 A | 12/1999 | Bell | 604/164.01 |
| 6,015,397 A | 1/2000 | Elson et al. | 604/192 |
| 6,036,675 A | 3/2000 | Thorne et al. | 604/232 |
| 6,149,629 A | 11/2000 | Wilson et al. | 604/198 |
| 6,171,284 B1 | 1/2001 | Kao et al. | 604/192 |
| RE37,110 E | 3/2001 | Hollister | 206/365 |
| 6,224,576 B1 | 5/2001 | Thorne et al. | 604/198 |
| RE37,252 E | 7/2001 | Hollister | 206/364 |
| 6,254,575 B1 | 7/2001 | Thorne, Jr. et al. | 604/198 |
| 6,280,420 B1 | 8/2001 | Ferguson et al. | 604/198 |
| 6,334,857 B1 | 1/2002 | Hollister et al. | 604/263 |
| 6,582,397 B2 | 6/2003 | Alesi et al. | 604/110 |
| 6,635,032 B2 | 10/2003 | Ward, Jr. | 604/192 |
| 2001/0039401 A1 | 11/2001 | Ferguson et al. | 604/198 |
| 2002/0072716 A1 | 6/2002 | Barrus et al. | 604/192 |
| 2003/0004465 A1 | 1/2003 | Ferguson et al. | 604/198 |

FOREIGN PATENT DOCUMENTS

| | | |
|---|---|---|
| EP | 0 344 606 A2 | 12/1989 |
| EP | 0 457 477 B1 | 11/1991 |
| EP | 0 485 345 B1 | 5/1992 |
| EP | 0 585 391 B1 | 11/1992 |
| EP | 0 533 308 A1 | 3/1993 |
| EP | 0 626 924 B1 | 1/1994 |
| EP | 0 654 281 B1 | 9/1994 |
| EP | 0 597 857 B1 | 7/1995 |
| EP | 0 705 613 B1 | 4/1996 |
| EP | 0 713 710 A1 | 5/1996 |
| EP | 0 815 890 A2 | 9/1997 |
| EP | 0 815 888 A2 | 10/1997 |
| EP | 0 807 443 A2 | 11/1997 |
| EP | 0 832 659 A2 | 12/1997 |
| EP | 0 819 441 A1 | 1/1998 |
| EP | 0 603 365 B1 | 2/1998 |
| EP | 0 832 660 A2 | 4/1998 |
| EP | 1 092 443 A2 | 4/2001 |
| EP | 1 116 493 A1 | 7/2001 |
| GB | 1 233 302 | 5/1971 |
| GB | 2 283 429 A | 5/1995 |
| GB | 2 369 779 A | 6/2002 |
| JP | 10-076007 | 3/1998 |
| JP | 10-127765 | 5/1998 |
| WO | WO 87/07162 | 12/1987 |
| WO | WO 89/07955 | 9/1989 |
| WO | WO 93/17732 | 9/1993 |
| WO | WO 94/19036 | 9/1994 |
| WO | WO 97/31666 | 9/1997 |
| WO | WO 98/07463 | 2/1998 |
| WO | WO 98/10816 | 3/1998 |
| WO | WO 98/11928 | 3/1998 |
| WO | WO 98/13081 | 4/1998 |
| WO | WO 99/59660 | 11/1999 |
| WO | WO 00/16832 | 3/2000 |
| WO | WO 00/38765 | 7/2000 |
| WO | WO 01/32241 A1 | 5/2001 |
| WO | WO 01/32244 A1 | 5/2001 |
| WO | WO 01/36030 A1 | 5/2001 |

* cited by examiner

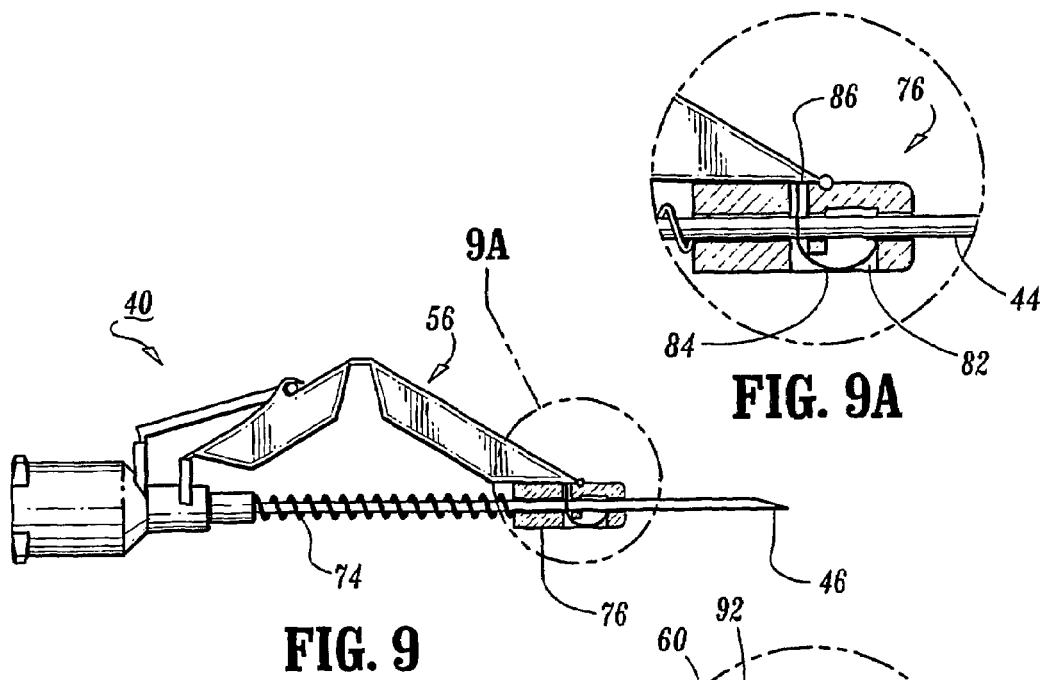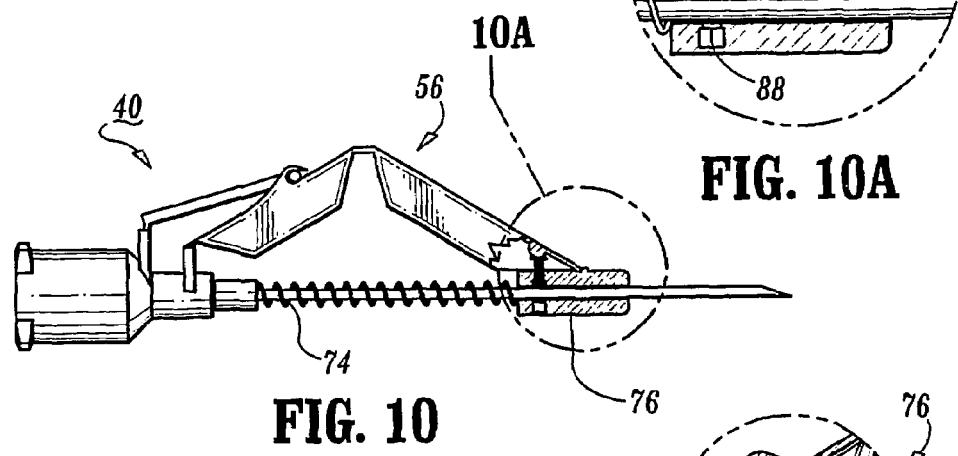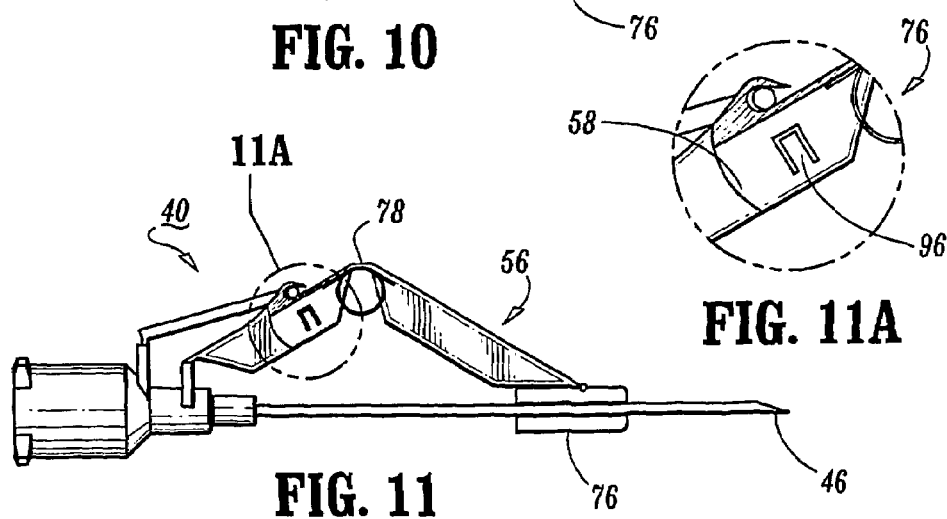

PASSIVE SAFETY SHIELD

CROSS-REFERENCE TO RELATED APPLICATION

This patent application claims priority to U.S. Provisional Application Ser. No. 60/272,864 filed in the U.S. Patent and Trademark Office on Mar. 2, 2001 by Fiser et al., the entire contents of which being hereby incorporated by reference herein.

BACKGROUND

1. Technical Field

The present disclosure generally relates to safety apparatus for medical needles, and more particularly, to safety apparatus that are extensible and automatically deployed to prevent hazardous exposure to a medical needle.

2. Background of the Related Art

Cross-contamination and infection from potentially fatal diseases transmitted by inadvertent needle sticks have resulted in the development of a wide variety of safety medical needle devices used in the areas of I.V. therapy, venipuncture, phlebotomy, syringes and specialty medical needle devices. See, e.g., U.S. Pat. Nos. 5,348,544, 5,584,818, 5,735,827, 5,738,665, 5,910,130 and 5,925,020. These diseases include the HIV virus, several strains of hepatitis and other blood and body fluid borne diseases.

Safety medical devices, similar to those exemplified above, require action from a practitioner performing an infusion, blood collection, etc., to deploy needle protection. For example, such devices may require a flip tab release, manually activated actuator, force application to a plunger rod, etc., to enclose a needle subsequent to a medical procedure. These type devices disadvantageously require forced activation of the device and can result in uncontrolled manipulation, faulty operation and a dangerous condition to the practitioner, thereby defeating the intended purpose of the safety device.

Another disadvantage of prior art devices includes actuation of needle protection as a conscious decision and within the purview of the practitioner. Consequently, the safety device may not be employed resulting in non-assurance of compliant safety practices. Further, some devices disadvantageously require complete expulsion of all syringe contents prior to deployment of needle protection. Still others include excessive or unexpected forces during deployment of needle protection based on uncontrolled forward movement of a shield or the like. This drawback may result in injury to the practitioner and patient.

It would therefore be desirable to overcome the disadvantages and drawbacks of the prior art by providing a safety apparatus for medical needles which is extensible and automatically deployed to prevent hazardous exposure to a medical needle.

SUMMARY

Accordingly, a safety apparatus for medical needles which is extensible and automatically deployed to prevent hazardous exposure to a medical needle is provided. One of the advantages of the present disclosure is a reduction of needle stick injuries involving contaminated needles. This results in increased safety to practitioners and patients during medical procedures for treatment and diagnosis of patients, such as, for example, combative patients, etc.

Another advantage of the present disclosure is assured compliance with safety practices because of automatic deployment.

It is contemplated that the safety apparatus disclosed provides structure which is maintained in a ready to use position with safety features being activated automatically during a medical procedure. It is further contemplated that the safety apparatus is adaptable to standard infusion and blood collection devices, such as, for example, luer type syringes. It is envisioned that the safety apparatus of the present disclosure does not require forced activation from the practitioner for deployment. Alternatively, the safety apparatus may include manual override features.

In one particular embodiment, in accordance with the principles of the present disclosure, a safety apparatus is provided. The safety apparatus includes a needle hub having an arm extending therefrom and an extensible frame connected to the needle hub. The extensible frame includes a proximal segment that is hingedly connected to a distal segment. It is contemplated that the extensible frame may be joined by an intermediate segment(s) disposed between the proximal segment and the distal segment. It is envisioned that the extensible frame can include one or a plurality of segments.

The extensible frame is resiliently biased from a retracted position to an extended position, wherein the arm releasably engages the proximal segment to fix the extensible frame in a position between the retracted position and the extended position. It is contemplated that the arm may extend from the proximal segment and releasably engage the needle hub, extend from the needle hub and releasably engage the distal segment, extend from the distal segment and releasably engage the needle hub, extend from the proximal segment and releasably engage the distal segment, extend from the distal segment and releasably engage the proximal segment, or, alternatively, extend from any intermediate, proximal or distal segment and releasably engage any other intermediate, proximal or distal segment.

In an alternate embodiment, the safety apparatus includes an extensible frame including a proximal segment which is hingedly connected to a distal segment. A resilient member is coupled to the proximal segment and the distal segment. The resilient member is configured to bias the extensible frame from a retracted position to an extended position.

In an alternate embodiment, the safety apparatus includes a needle hub and an extensible frame connected thereto. The extensible frame including a proximal segment and a distal segment. The extensible frame being resiliently biased from a retracted position to an extended position. An arm member extends from any one of the needle hub and segments. The arm member releasably engages any other one of the needle hub and segments to fix the extensible frame in a position between the retracted position and the extended position.

A method for infusing fluids to a subject is disclosed. The method includes the steps of: providing a safety apparatus, similar to those described; attaching a needle hub of the safety apparatus to a syringe; removing a sheath cap of the safety apparatus to expose a needle cannula; drawing liquid via the needle cannula into the syringe; removing a sheath from the safety apparatus; performing an infusion with the syringe and safety apparatus; removing the needle cannula from a subject such that a needle cover automatically encloses the distal end of the needle cannula.

In an alternate embodiment, the method infuses fluids to a subject with a single needle including the steps of: providing a safety apparatus including a needle hub configured to support a needle cannula, an extensible frame, connected to the needle hub, including at least one segment and being resiliently biased from a retracted position to an extended position to actuate an automatic locking cover extending from the segment, and a sheath having a sheath cap and being configured to support the safety apparatus; attaching the needle hub to a syringe, removing the sheath cap to expose a length of the needle cannula; inserting the needle cannula in a vial to draw liquid, via the needle cannula, into the syringe such that the sheath prevents the automatic locking cover from actuating; removing the sheath from the safety apparatus without actuating the automatic locking cover; performing an infusion with the syringe and safety apparatus; and removing the needle cannula from the subject such that the locking cover automatically encloses a distal end of the needle cannula The present disclosure is designed to automatically shield hypodermic, blood collection, trocar, etc., needles and cannulas upon removal from a patient to protect healthcare practitioners from inadvertent needlesticks and associated potential blood borne pathogen exposure. The safety apparatus may lock in an irreversible manner upon full deployment.

BRIEF DESCRIPTION OF THE DRAWINGS

The objects and features of the present disclosure are set forth with particularity in the appended claims. The present disclosure, as to its organization and manner of operation, together with further objectives and advantages may be understood by reference to the following description, taken in connection with the accompanying drawings, in which:

FIG. 9 is a side view, in part cross section, of the safety apparatus shown in FIG. 6;

FIG. 9A is an enlarged view of the indicated area of detail shown in FIG. 9;

FIG. 10 is a side view, in part cross section, of an alternate embodiment of the safety apparatus shown in FIG. 9;

FIG. 10A is an enlarged view of the indicated area of detail shown in FIG. 10;

FIG. 11 is a side view, in part cross section, of an alternate embodiment of the safety apparatus shown in FIG. 6;

FIG. 11A is an enlarged view of the indicated area of detail shown in FIG. 11;

DETAILED DESCRIPTION OF EXEMPLARY EMBODIMENTS

Figure 1:
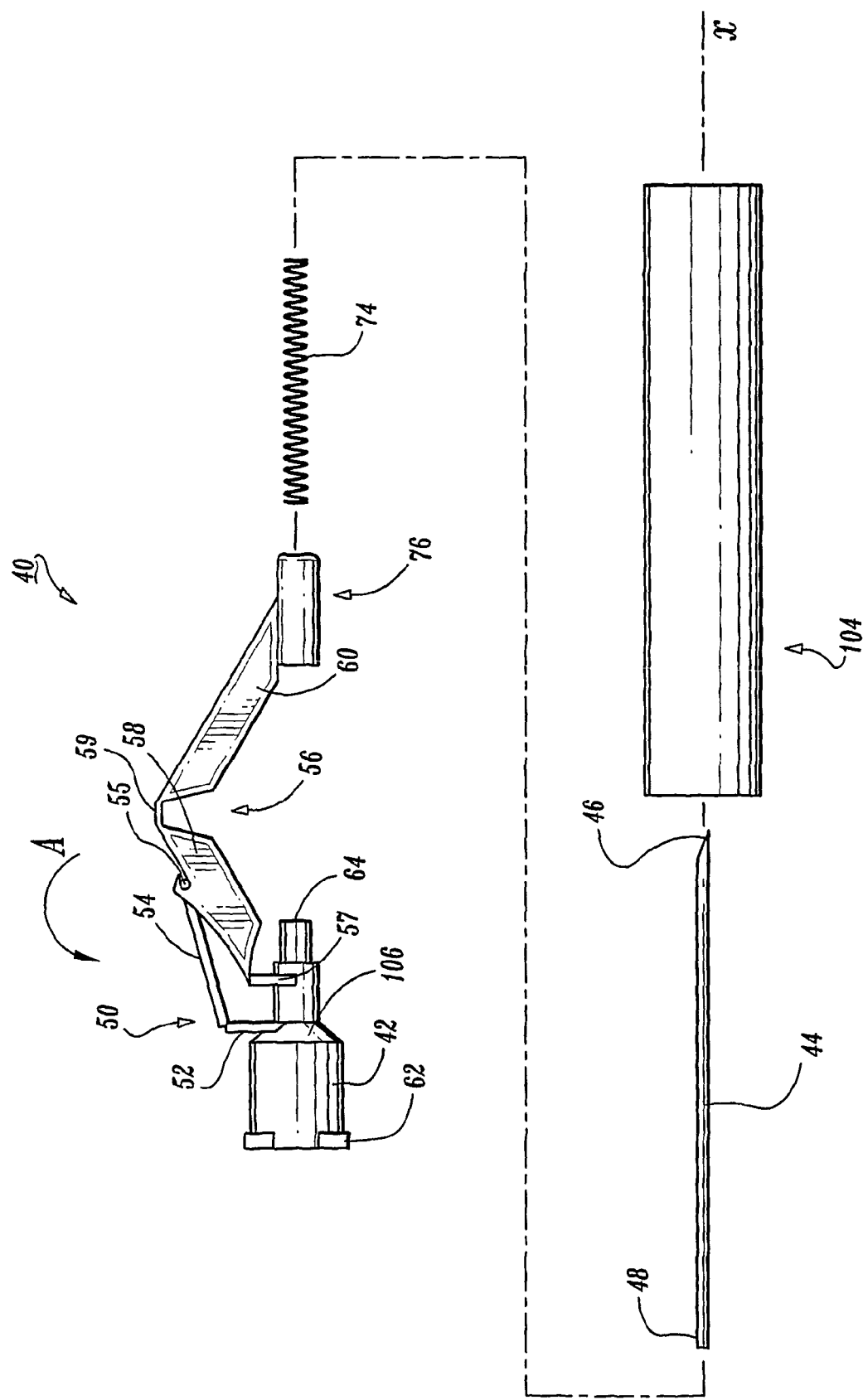
FIG. 1 is a side view, with parts separated, of one particular embodiment of a safety apparatus, in accordance with the principles of the present disclosure.
Figure 2:
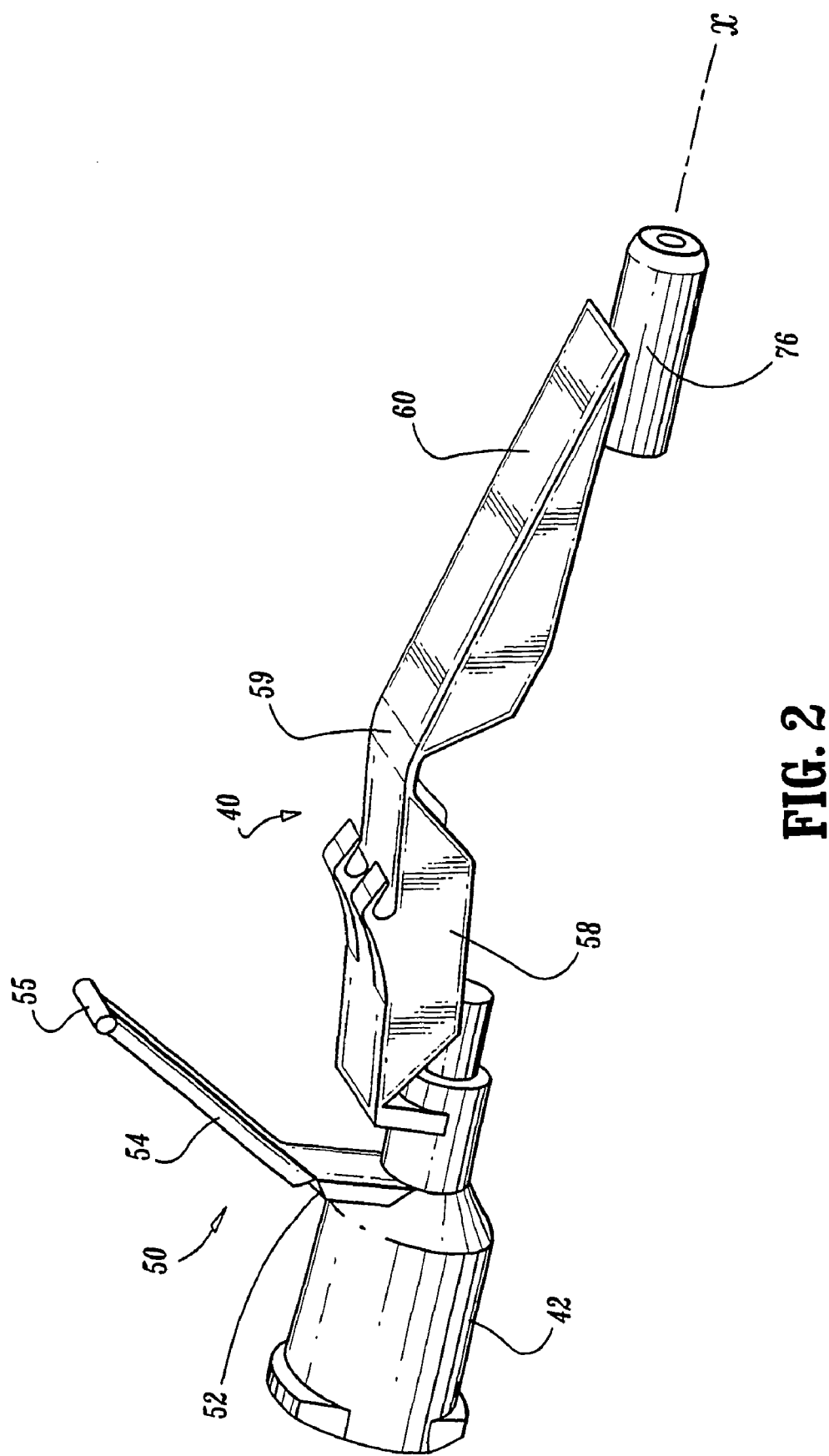
FIG. 2 is a side perspective view of the safety apparatus shown in FIG. 1, assembled.

The exemplary embodiments of the safety apparatus and methods of operation disclosed are discussed in terms of medical needles for infusion of fluids and fluid collection, and more particularly, in terms of a medical needle apparatus, employing a needle cannula, that is extensible and automatically deployed to prevent hazardous exposure to the needle cannula, including, for example, inadvertent needle stick. It is contemplated that the needle cannula may be shielded during use including storage, transport, fluid infusion and/or collection, subsequent thereto, etc. It is envisioned that the present disclosure, however, finds application to a wide variety of cannula needles and devices for the infusion of preventive medications, medicaments, therapeutics, etc. to a subject. It is also envisioned that the present disclosure may be employed for collection of body fluids, including, those employed during procedures relating to venipuncture, phlebotomy, digestive, intestinal, urinary, veterinary, etc.

In the discussion that follows, the term "proximal" refers to a portion of a structure that is closer to a practitioner, and the term "distal" refers to a portion that is further from the practitioner. As used herein, the term "subject" refers to a patient that receives infusions or has blood and/or fluid collected therefrom using the safety apparatus. According to the present disclosure, the term "practitioner" refers to an individual administering an infusion, performing fluid collection, installing or removing a needle cannula from a safety shield apparatus and may include support personnel.

The following discussion includes a description of the safety apparatus, followed by a description of the method of operating the safety apparatus in accordance with the present disclosure. Reference will now be made in detail to the exemplary embodiments of the disclosure, which are illustrated in the accompanying figures.

Turning now to the figures wherein like components are designated by like reference numerals throughout the several views. Referring initially to FIGS. 1-5, there is illustrated a safety apparatus 40, constructed in accordance with the principals of the present disclosure, including a needle hub 42 configured to support a medical needle cannula 44 having a sharpened distal end 46. Needle cannula 44 is supported by needle hub 42 at a proximal end 48 thereof and defines a longitudinal axis x. Needle hub 42 has a locking arm 50 extending therefrom. Locking arm 50 includes a first member 52 and a second member 54 hingedly attached thereto. First member 52 is affixed to needle hub 42 and second member 54 is movable relative to first member 52, as will be discussed. It is envisioned that locking arm 50 may include a plurality of members. Locking aim 50 has a locking pin 55 extending from a distal end of second member 54 to facilitate fixing safety apparatus 40 in a desired position, as will be discussed.

Figure 5:
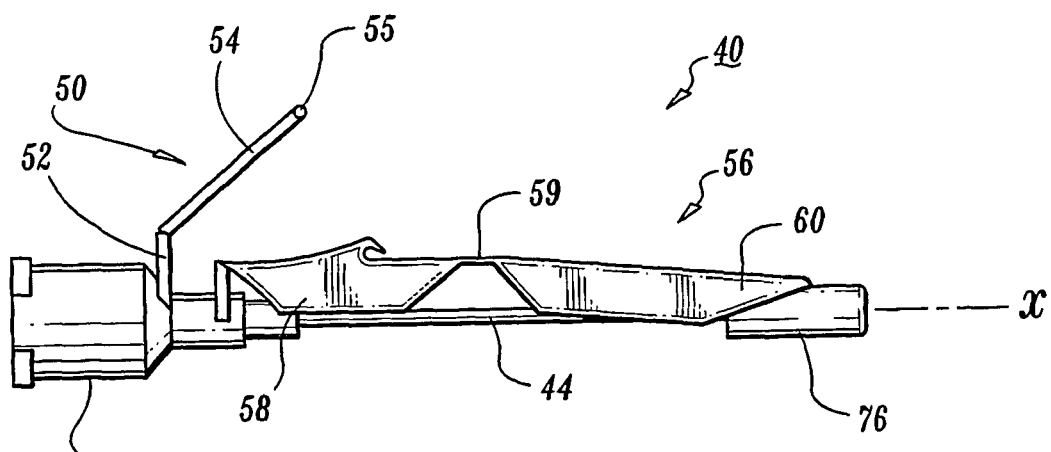
FIG. 5 is a side view of the safety apparatus shown in FIG. 1, assembled, in the extended position.

An extensible frame 56 is connected to needle hub 42. Extensible frame 56 includes a proximal segment 58, mounted with needle hub 42 via stem 57, which is connected via hinge 59 to a distal segment 60. Extensible frame 56 is resiliently biased from a retracted position (FIG. 4) to an extended position (FIG. 5). It is contemplated that the hinged connection of extensible frame 56 may be living hinges, pinned hinges, etc., or alternatively, may be movably connected by other structure such as, ball joint, etc. It is further contemplated that extensible frame 56 may be joined by an intermediate segment(s) disposed between proximal segment 58 and distal segment 60. It is envisioned that extensible frame 56 can include one or a plurality of segments.

Locking aim 50 releasably engages proximal segment 58 to fix extensible frame 56 in a ready-to-use position (FIG. 3) between the retracted position and the extended position. One of the advantages of safety apparatus 40 is extensible flame 56 which is automatically deployed, as will be discussed, to prevent hazardous exposure to a needle by providing an adequate and reliable safety apparatus upon removal from an insertion site. Thus, another advantage of the present disclosure is that safety apparatus 40 is actuated without the necessity of a practitioner applying a force to safety apparatus 40 during removal, resulting in a higher degree of safety to the practitioner and subject.

Safety apparatus 40 is contemplated for use in the field of medical fluid infusion and/or collection. More particularly, safety apparatus 40 is envisioned to be a single infusion/collection, disposable needle device employing, among other things, safety features having shielding capabilities to prevent inadvertent sticking or punctures of practitioners and subjects, as well as uniform and dependable movement of extensible frame 56 during a procedure and a locking mechanism for reliable use. The above advantages, among others, realized from the present disclosure are attained through the disclosed safety apparatus 40, which is extensible to a protective configuration, as discussed herein below. These features of the present disclosure advantageously facilitate a safe infusion and/or collection of fluids and prevent inadvertent needle stick of a practitioner and subject.

The component parts of safety apparatus 40 may be fabricated from a material suitable for medical applications, such as, for example, polymerics or metals, such as stainless steel, depending on the particular medical application and/or preference of a practitioner. Semi-rigid and rigid polymerics are contemplated for fabrication, as well as resilient materials, such as molded medical grade polypropylene. It is envisioned that the component parts of safety apparatus 40 may be injection molded, by using, for example, synthetic resinous material. However, one skilled in the art will realize that other materials and fabrication methods suitable for assembly and manufacture, in accordance with the present disclosure, also would be appropriate. Safety shield apparatus 40 may be integrally assembled of its constituent parts. Alternatively, portions of safety shield apparatus 40 can be monolithically formed and assembled therewith. Safety apparatus 40 is contemplated for adaptability with existing blood collection tube holders, luer lock syringe, luer slip syringes, etc.

Hub 42 includes a standard luer lock connection 62 and a bonding area 64 for attachment with proximal end 48 of needle 44. Locking arm 50 and proximal segment 58 are affixed to needle hub 42 via first member 52 and stem 57, respectively, however, these components may be directly mounted to needle hub 42. Locking pin 55 of locking arm 50 has a cylindrical configuration and extends transverse to longitudinal axis x. Locking pin 55 is employed to releasably fix extensible frame 56 in the ready to use position (FIG. 3) and prevent actuation of the safety features of safety apparatus 40. It is contemplated that locking arm 50 may extend from proximal segment 58 and releasably engage needle hub 42, extend from needle hub 42 and releasably engage distal segment 60, extend from distal segment 60 and releasably engage needle hub 42, extend from proximal segment 58 and releasably engage distal segment 60, extend from distal segment 60 and releasably engage proximal segment 58, or, alternatively, extend from any intermediate, proximal or distal segment and releasably engage any other intermediate, proximal or distal segment.

Figure 6:
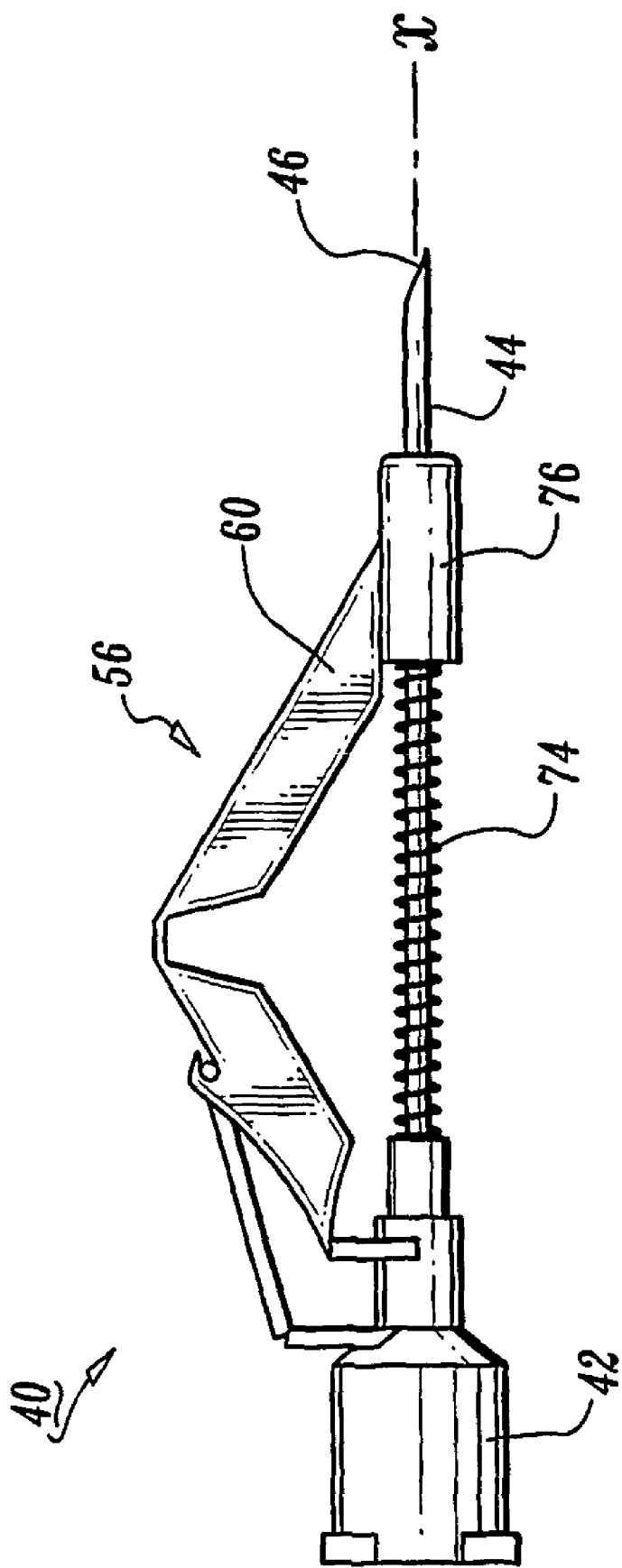
FIG. 6 is a side view of the safety apparatus shown in FIG. 1, assembled, illustrating a coil spring.

Referring to FIG. 6, extensible frame 56 is resiliently biased via a coil spring 74 disposed about needle 44 along longitudinal axis x. Coil spring 74 engages distal segment 60 and needle hub 42 to provide a biasing force that causes extensible frame 56 to automatically extend to prevent hazardous exposure to needle 44. Coil spring 74 engages a safety tip cover 76 of distal segment 60. Safety tip cover 76 extends from distal segment 60 to substantially enclose distal point 46 of needle 44 and prevent exposure thereto.

Figure 7:
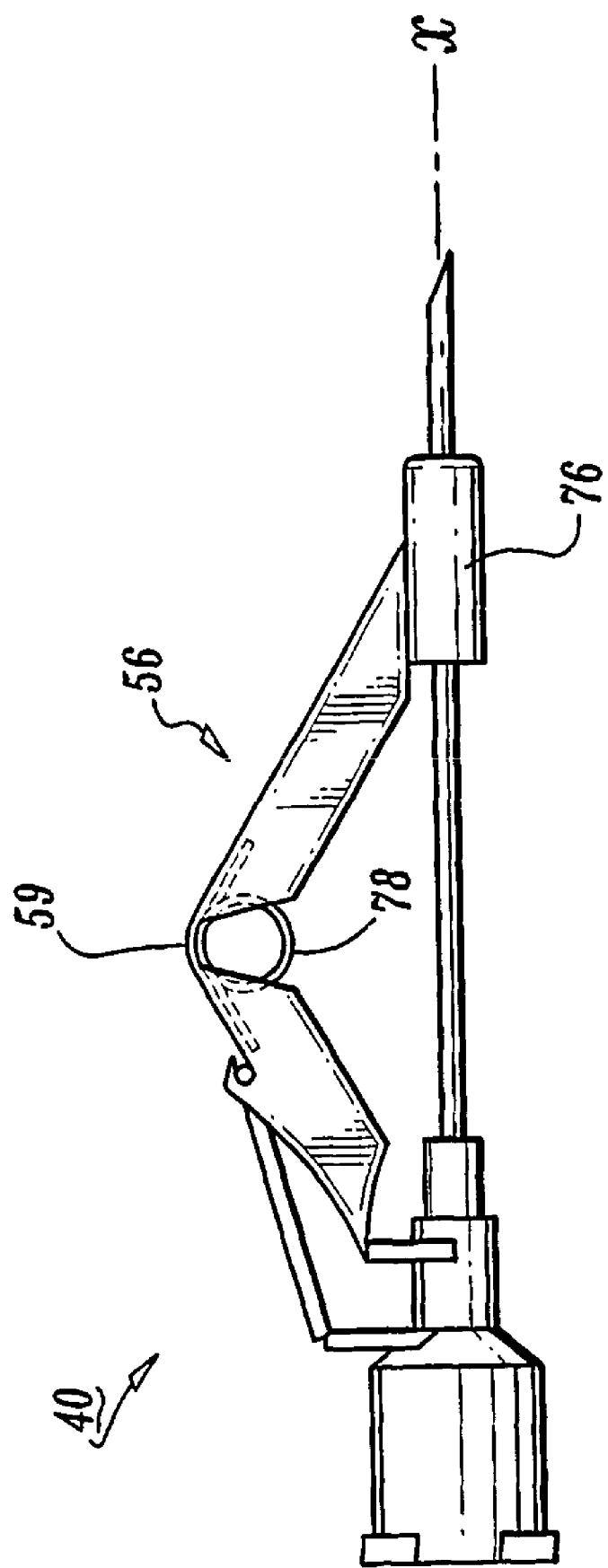
FIG. 7 is a side view of an alternate embodiment of the safety apparatus shove in FIG. 6 illustrating a torsion spring.
Figure 8:
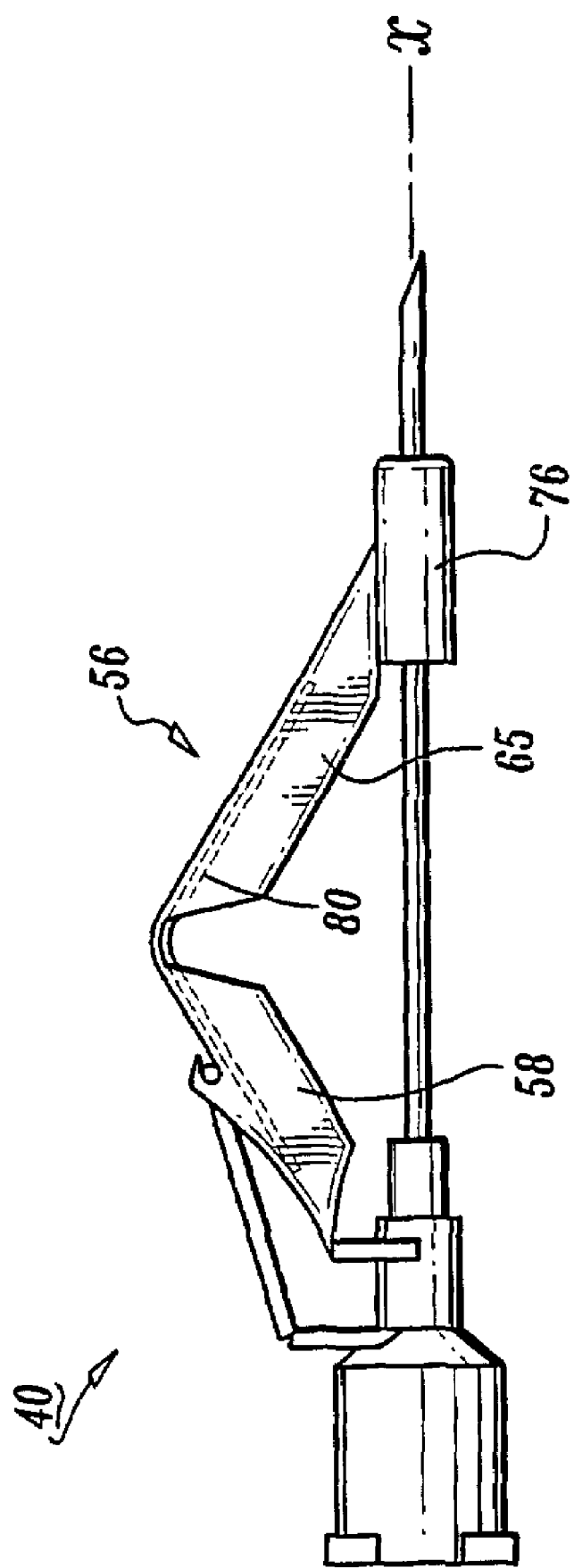
FIG. 8 is a side view of an alternate embodiment of the safety apparatus shown in FIG. 6 illustrating a leaf spring.

It is contemplated that other springs may be used to resiliently bias extensible frame 56 and activate safety tip cover 76. For example, referring to FIG. 7, a torsion spring 78 mounted adjacent hinge 59 of extensible frame 56 may be used. Alternatively, as shown in FIG. 8, a leaf spring 80 mounted with proximal segment 58 and distal segment 60 can be used to bias extensible frame 56 from the retracted position to the extended position. It is contemplated that the spring employed provides low resistance to the activation of safety apparatus 40 while allowing adequate travel of safety tip cover 76 and force to assure activation of the lock mechanism.

Referring back to FIGS. 3, 3A, 4 and 4A, proximal segment 58 includes a pair of retaining pockets 66 formed in an outer surface thereof. It is contemplated that retaining pockets 66 may be monolithically formed or integrally mounted with proximal segment 58. Retaining pockets 66 are defined, in part, by flaps 68 such that retaining pockets 66 from a "tear drop" shape. Retaining pockets 66 are configured to receive and releasably retain locking pin 55 formed at a distal end of second member 54. Flaps 68 prevent undesired release of locking pin 55 from pockets 66.

Flaps 68 may have other configurations for releasably retaining locking pin 55, such as, for example, linear, bow shaped, etc. It is also contemplated that a single retaining pocket could be utilized with the embodiments of the present disclosure.

Flaps 68 are flexible such that upon application of a sufficient force, as will be discussed, locking pin 55 engages flaps 68. Flaps 68 elastically deform, allowing locking pin 55 to exit retaining pockets 66. Upon exit of locking pin 55, flaps 68 return to a non-deformed position, due to their elasticity. This configuration sufficiently closes retaining pockets 66 to prevent re-entry of locking pin 55.

For example, as an infusion is performed and distal end 46 of needle 44 is inserted into a subject, rearward axial movement of a safety tip cover 76, extending from distal segment 60, along needle 44, causes extensible frame 56 to retract towards the retracted position. Proximal segment 58 moves generally rearward and rotates, as shown by arrow A in FIG. 1, such that locking pin 55 is forced to exit retaining pockets 66 as facilitated by movable second member 54. This cooperative movement forces locking pin 55 to elastically deform flaps 68. Locking pin 55 is released from retaining pockets 66 as needle 44 is further inserted and extensible frame 56 moves to the retracted position. Flaps 68 return to their undeformed state to prevent re-entry of locking pin 55, exemplifying pockets 66 uni-directional feature. The advantageous feature of uni-directional retaining pockets 66 maintains extensible frame 56 in a ready to use position. Pockets 66 do not require rotation for activation of the safety features. This design prevents the activated safety apparatus 40 from falling back into the ready to use position.

It is contemplated that safety apparatus 40 may have one or a plurality of retaining pockets 66. It is further contemplated that retaining pockets 66 may be variously disposed with extensible frame 56, needle hub 42, etc., and flaps 68 formed of various flexibilities according to the particular requirements of a medical needle application and/or preference of the practitioner. Pockets 66 have a uni-directional releasable locking feature that may be easily activated and difficult to reengage. Alternative releasably engageable structure may be used, such as, for example, ball and socket, frangible. etc.

Safety tip cover 76 is hingedly attached with distal segment 60 to allow relative movement therebetween during movement of safety tip cover 76 along longitudinal axis x. Safety tip cover 76 travels proximally to the retracted position and distally along needle 44 to the extended position of extensible frame 56. In the extended position, safety tip cover 76 is configured to substantially enclose distal end 46 of needle 44.

Referring to FIGS. 9 and 9A, needle tip cover 76 has a length sufficient to enclose distal end 46 and is connected to a distal end of coil spring 74 to facilitate bias of extensible frame 56. Safety tip cover 76 defines a cavity 82 which supports a biasing clip, such as, for example, trap 84. Trap 84 is mounted within cavity 82 so that trap 84 bows outward from safety tip cover 76 upon engagement with needle 44. As safety tip cover 76 extends to the extended position, trap 84 is released from lateral engagement with needle 44 and is free to slide within a pin cavity 86 of safety tip cover 76. The resilient bias of trap 84 causes trap 84 to engage pin cavity 86 and lockingly prevent distal end 46 front passing through safety tip cover 76. This looking feature of safety apparatus 40 prevents hazardous exposure to needle 44.

In an alternate embodiment, as shown in FIGS. 10 and 10A, safety tip cover 76 includes a transverse cavity 88 configured for receipt of a pin 90 to facilitate locking extensible frame 56 in the extended position. Distal segment 60 has a member 92 formed adjacent safety tip cover 76. Member 92 is attached to pin 90 to facilitate slidable movement within transverse cavity 88. As distal segment 60 is movable between the retracted position and the extended position, pin 90 moves from a withdrawn position to an engaged position. For example, as needle 44 initially passes through safety tip cover 76, pin 90 is caused to withdraw from transverse cavity 88, with extensible frame 56 retracted.

In the extended position, member 92 forces pin 90 into transverse cavity 88 and lockingly prevents distal end 46 from exiting safety tip cover 76. This configuration advantageously prevents hazardous exposure to needle 44.

Referring to FIGS. 11 and 11A, in another alternate embodiment, as extensible frame 56 extends to the extended position and safety tip cover 76 encloses distal end 46, a catch tab 96 disposed on an inner surface of proximal segment 58, engages needle 44. Catch tab 96 is a uni-directional lock that snaps about needle 44 when extensible frame 56 is in the extended position. This locking feature fixes extensible frame 56 in the extended position and advantageously prevents hazardous exposure to needle 44. Torsion spring 78, similar to that described with regard to FIG. 7, resiliently biases extensible frame 56 from the retracted position to the extended position. It is contemplated that catch tab 96 may be variously disposed with proximal segment 58, distal segment 60, or any intermediate segment employed.

Figure 12:
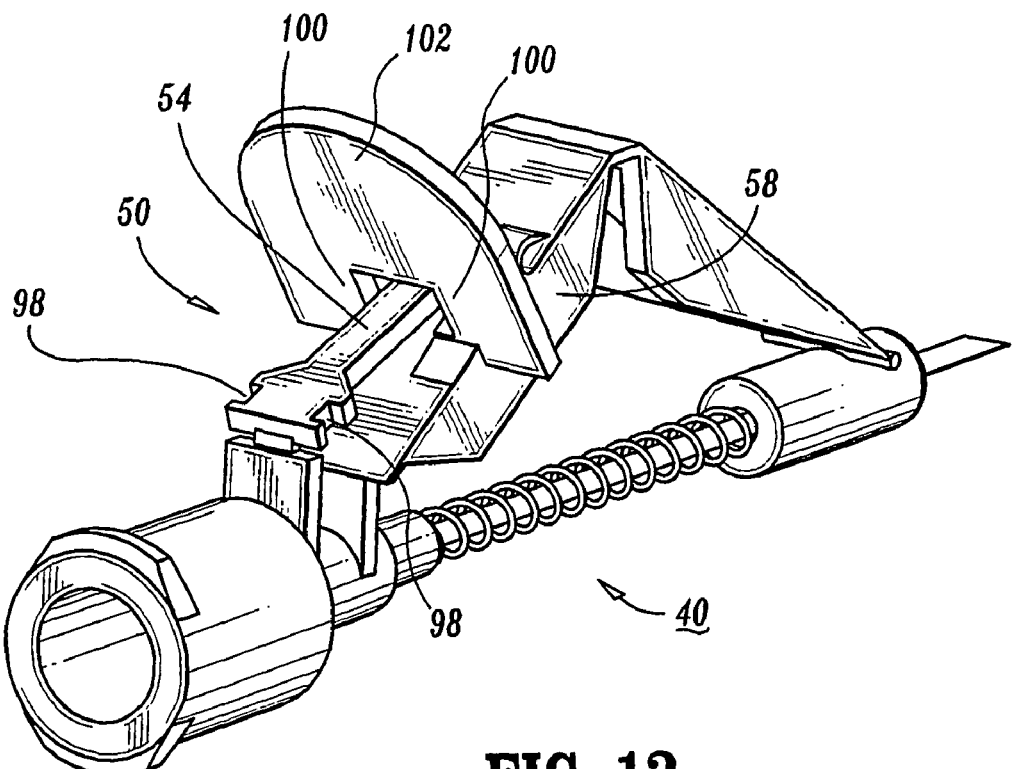
FIG. 12 is a side perspective view of an alternate embodiment of the safety apparatus shown in FIG. 6, in the flip-up position.
Figure 13:
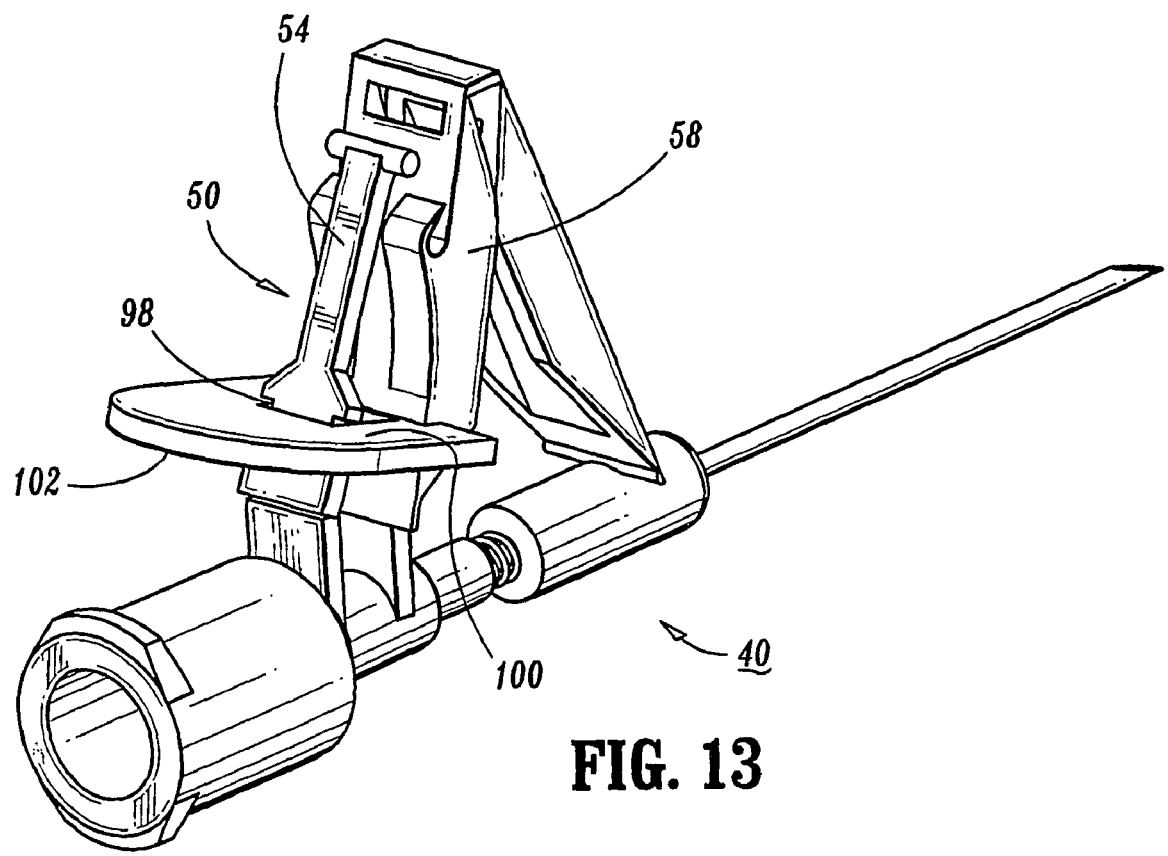
FIG. 13 is a side perspective view of the safety apparatus shown in FIG. 12, in the flip-down position.

Referring to FIGS. 12 and 13, in yet another alternate embodiment, safety apparatus 40 has a manual over-ride feature. This includes second member 54 of locking arm 50 having a pair of retaining tabs 98 formed therein. Retaining tabs 98 have a grooved configuration for receiving walls 100 of a push tab 102. Push tab 102 extends laterally from proximal segment 58 to engage retaining tabs 98.

Push tab 102 is movable relative to proximal segment 58 from a flip-up position (FIG. 12, extensible frame 56 in the ready to use position) to a flip-down position (FIG. 13, extensible frame 56 in the retracted position). When push tab 102 is depressed in the flip-down position, tab 102 overrides the safety features of safety apparatus 40 by engaging retaining tabs 98. This feature advantageously allows convenient needle placement for blood draws and other low angle injections where a safety shield is not desired. To reactivate safety apparatus 40, push tab 102 is pressed forward to the flip-up position. This disengages retaining tabs 98 and allows safety tip cover 76 to travel to a safe or locked position with extensible frame 56 extended.

Figure 14:
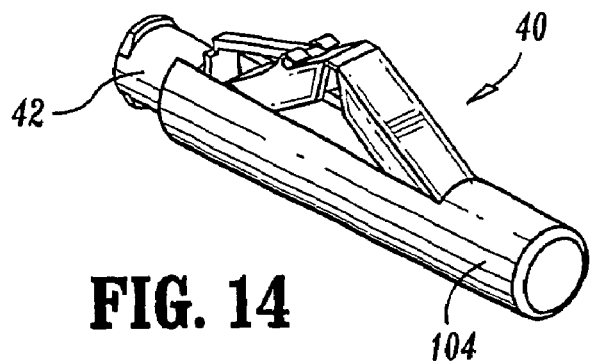
FIG. 14 is a side perspective view of the safety apparatus shown in FIG. 6 including a sheath.

Referring to FIGS. 1 and 14, safety apparatus 40 includes a sheath 104 configured as a protective cover attached to a base 106 of needle hub 42. Sheath 104 provides protection of needle 44 before use and/or inadvertent activation of safety tip cover 76.

Figure 15:
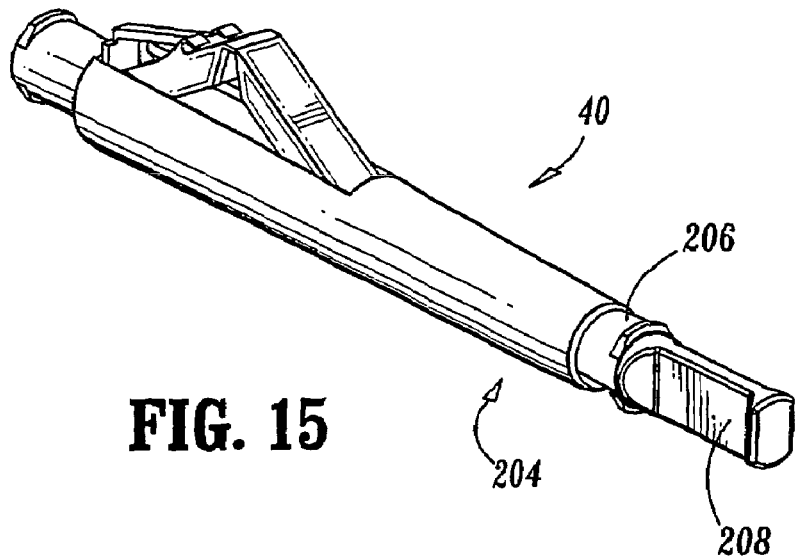
FIG. 15 is a side perspective view of the safety apparatus shown in FIG. 14 illustrating an alternate embodiment of the sheath.

Alternatively, as shown in FIG. 15, safety apparatus 40 includes a sheath 204, similar to sheath 104. Sheath 204 includes a blunt tip vial 206 mounted thereto. Blunt tip vial 206 includes an access pin 208 for piercing a rubber vial stopper 210 (not shown). To use sheath 204, the practitioner removes vial access pin 208 and pierces rubber vial stopper 210. Vial access pin 208 is disposed. Sheath 204 is attached to a syringe (not shown) by connecting luer components. After accessing fluids from vial stopper 210, blunt tip vial 206 is removed from the syringe using sheath 204 as a deinstallation tool. Safety apparatus 40 is attached to the filled syringe by connecting luer components.

Figure 16:
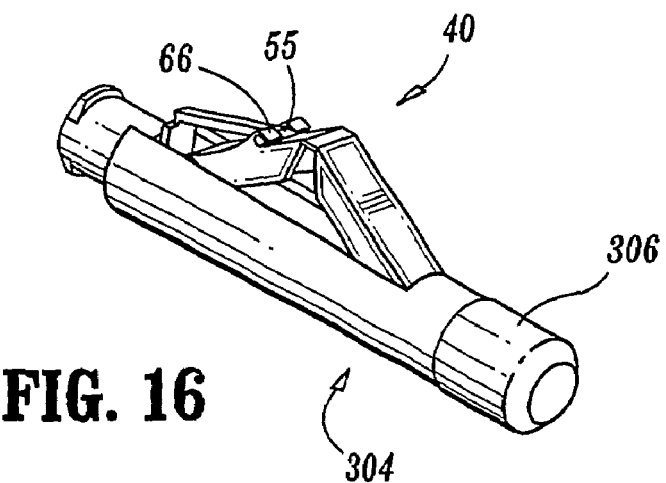
FIG. 16 is a side perspective view of the safety apparatus shown in FIG. 14 illustrating an alternate embodiment of the sheath.

Referring to FIG. 16, in another embodiment, safety apparatus 40 includes a sheath 304 including a sheath cap 306. Sheath 304 is mounted to needle hub 42 and extensible frame 56. Sheath cap 306 is mounted to a distal end of sheath 304. Sheath cap 306 is removed to allow needle 44 to penetrate a vial stopper 308 (FIGS. 25 and 26) without activating the safety features of safety apparatus 40. For example, upon engagement of safety tip cover 76 with vial stopper 308, extensible frame 56 is not actuated such that locking pin 55 does not exit retaining pockets 66. After removal of fluids from vial stopper 308, sheath 304 is removed for administering the injection with the safety features of safety apparatus 40 activated.

Figure 3A:
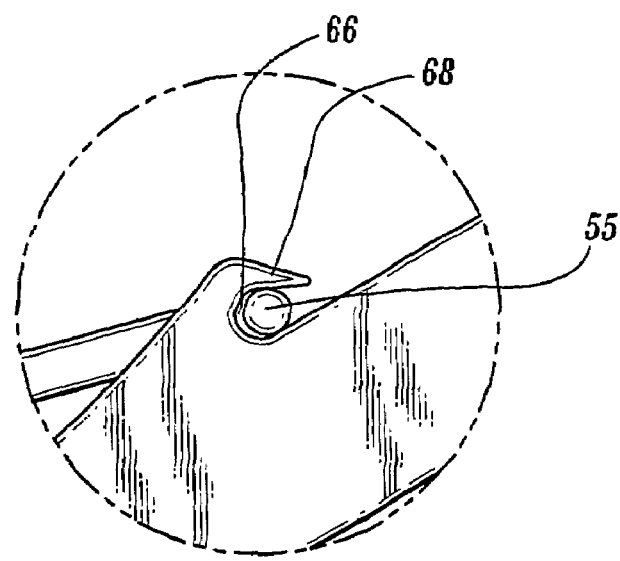
FIG. 3A is an enlarged view of the indicated area of detail shown in FIG. 3.
Figure 3:
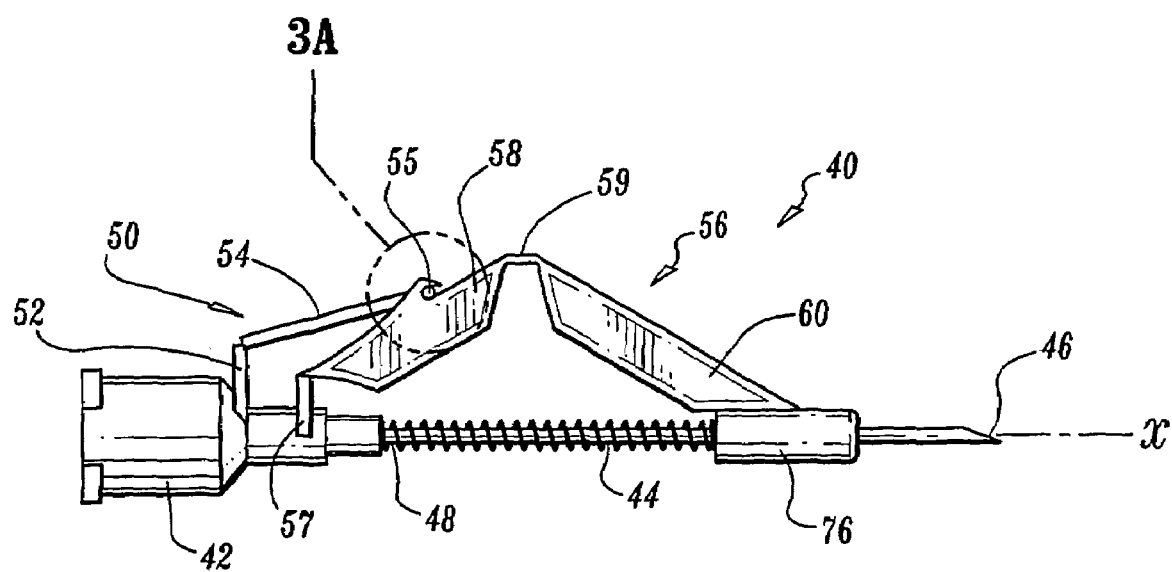
FIG. 3 is a side view of the safety apparatus shown in FIG. 1, assembled, in the ready to use position.
Figure 4A:
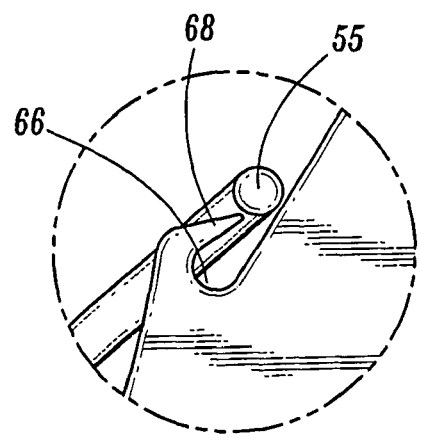
FIG. 4A is an enlarged view of the indicated area of detail shown in FIG. 4.
Figure 4:
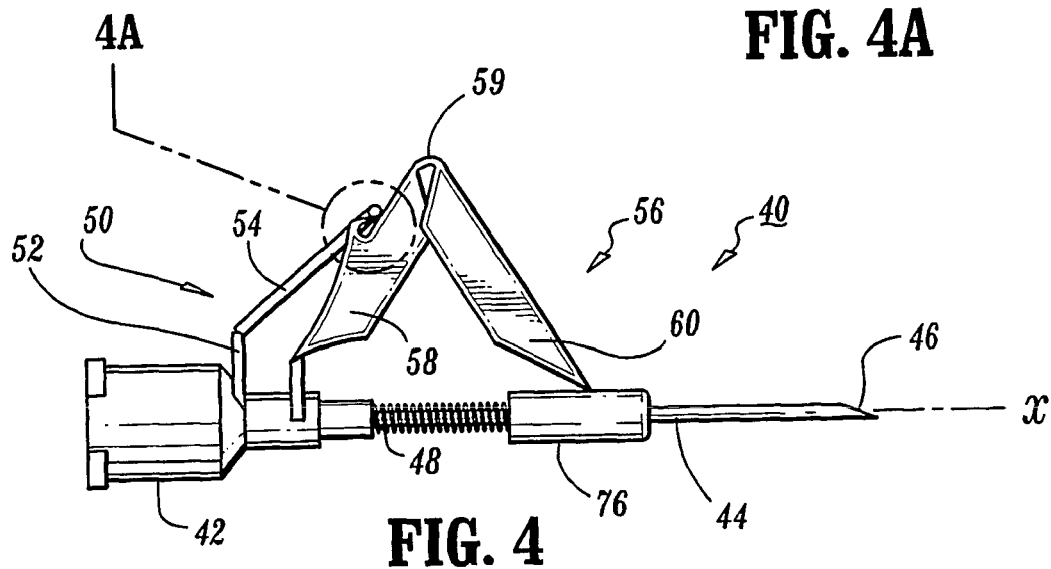
FIG. 4 is a side view of the safety apparatus shown in FIG. 1, assembled, in the retracted position.

In accordance with the present disclosure, safety tip cover 76 of safety apparatus 40 is movable to a plurality of positions along longitudinal axis x of needle 44. These positions include a ready to use position (FIG. 3). In the ready to use position, distal end 46 of needle 44 is exposed and locking pin 55 is configured to disengage from retaining pockets 66 upon rearward axial movement of safety tip cover 76. A retracted position, such as, for example, an in-use position (FIG. 4) illustrates locking pin 55 dislodged from retaining pockets 66 as a minimal force is applied to safety tip cover 76. Alternatively, as shown in FIGS. 12 and 13, a manually over ridden position allows the safety features of safety apparatus 40, for example, locking pin 55 and retaining pockets 66 cooperative disengagement, to be restrained until the practitioner, within her discretion, determines the procedure is complete and reactivates the safety features of safety apparatus 40.

Safety apparatus 40 also includes an extended position, such as, for example, a locked or safe position (FIG. 5) whereby the locking mechanisms, such as, for example, trap 84 is fully deployed and needle 44 is irreversibly protected, as discussed.

In operation, safety apparatus 40 may be properly sterilized and otherwise prepared for storage, shipment and use. Referring to FIGS. 17-20, in one particular embodiment, safety apparatus 40 employs sheath 104, discussed above. It is contemplated that operation of safety apparatus 40 with sheath 104 is for use with prefilled syringes or alternate vial access methods. Initially, safety apparatus 40 is removed from packaging. Safety apparatus 40 is attached, with sheath 104, to a syringe 108 filled with solution to be injected.

Figure 18:
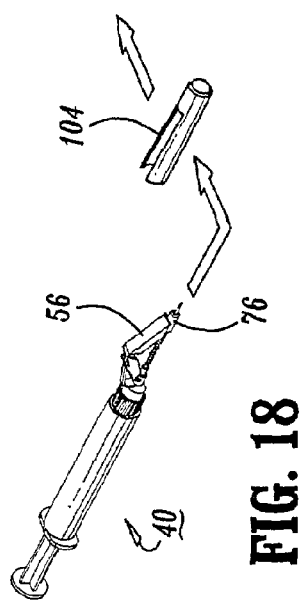
FIGS. 17-20 are perspective views illustrating operation of the safety apparatus shown in FIG. 14.
Figure 19:
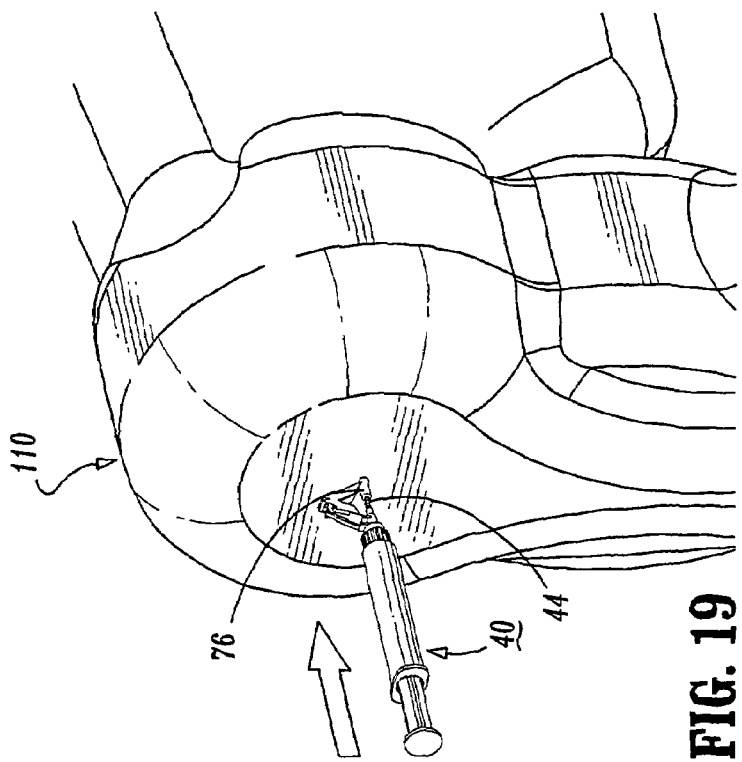
Figure 22:
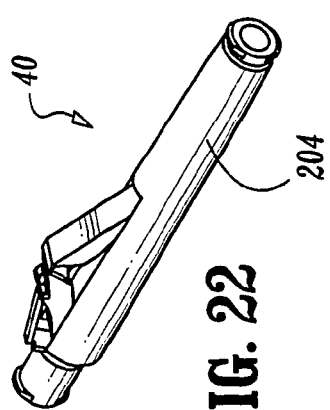
FIGS. 21-24 are perspective views illustrating operation of the safety apparatus shown in FIG. 15.

Sheath 104 is removed, as shown in FIG. 18. This positions extensible frame 56 in the ready to use position. An injection from syringe 108 to infuse fluids to a subject 110 is performed, as shown in FIG. 19. After needle 44 reaches a predetermined depth within subject 110, the face of safety tip cover 76 is forced rearward. Extensible frame 56 is in the retracted position. This releases locking pin 55 from uni-directional retaining pockets 66.

Figure 20:
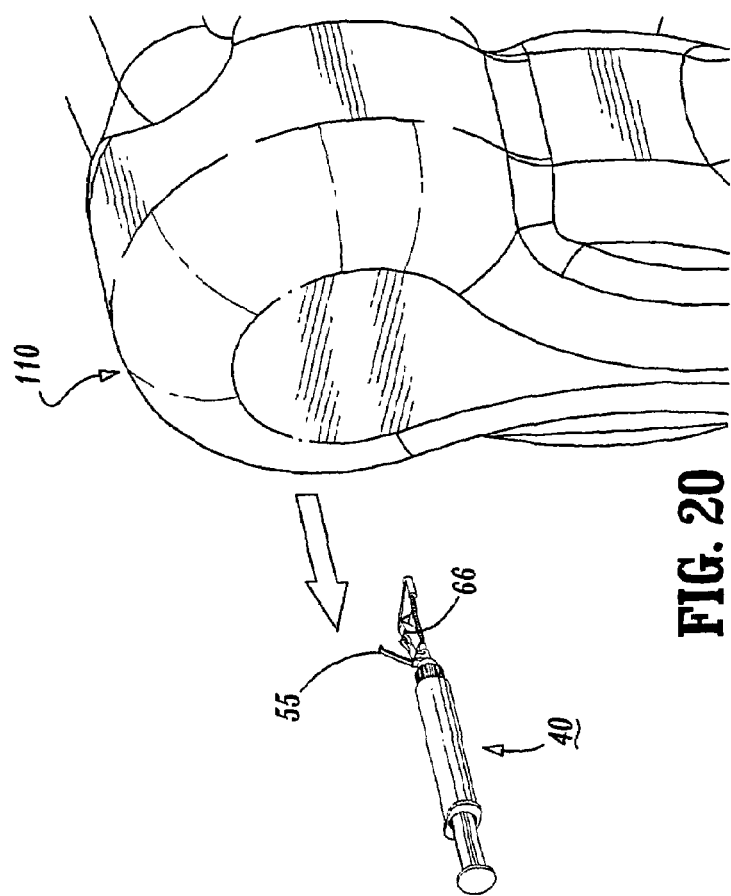
Figure 17:
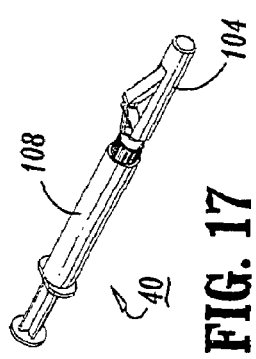

As needle 44 is removed, in the direction of arrow shown in FIG. 20, from the injection site of subject 110, extensible frame 56 travels with safety tip cover 76 to shield the shaft of needle 44 and enclose distal end 48. After complete extraction from the injection site, safety tip cover 76 extends slightly past distal end 46 positioning extensible frame 56 in the extended position such that safety apparatus 40 is in a disabled and locked condition.

Figure 23:
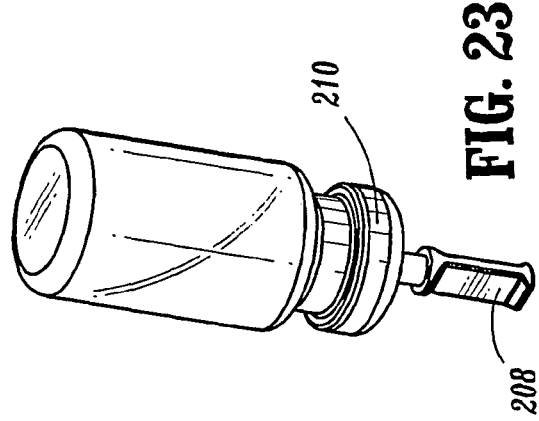
Figure 21:
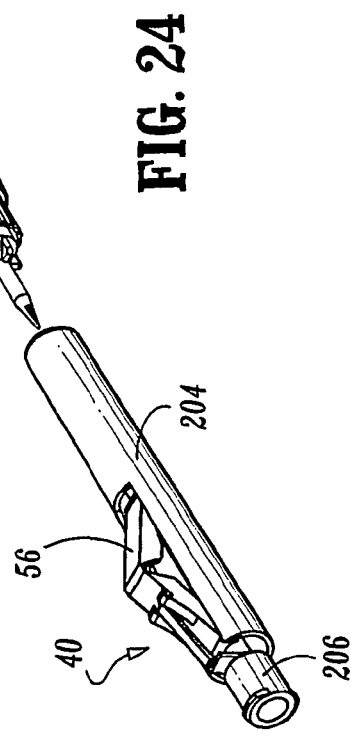

In an alternate embodiment, as shown in FIGS. 21-24, similar to that illustrated with regard to FIGS. 17-20, operation of safety apparatus 40 employs sheath 204, described above, and is contemplated for use with prefilled syringes or alternate vial access methods. Vial access pin 208 is removed from sheath 204, as shown in FIG. 21. Rubber vial stopper 210 is pierced and vial access pin 208 is disposed, as shown in FIG. 23.

Figure 24:
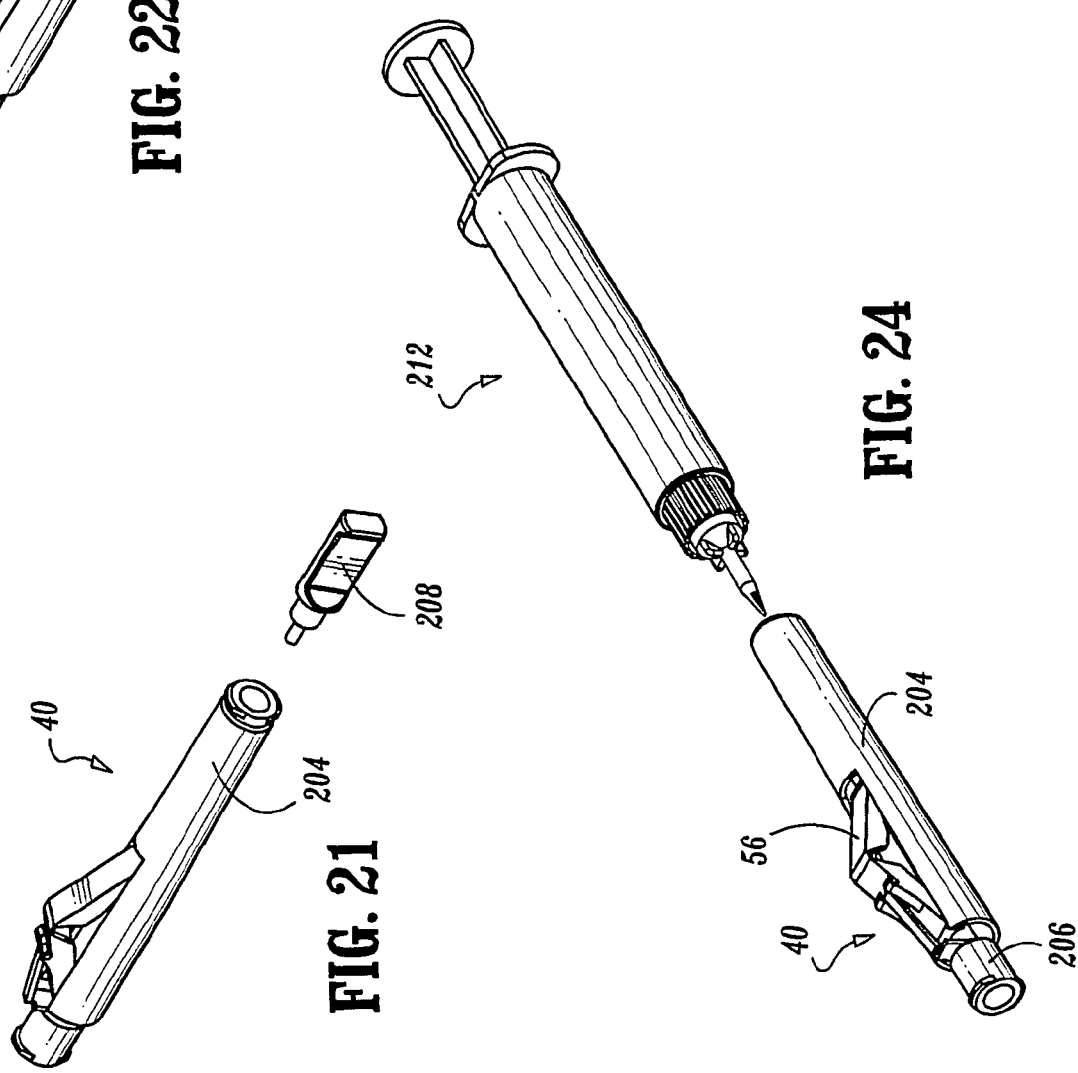

In an alternate embodiment, as shown in FIG. 24, blunt tip vial 206 is attached to a syringe and sheath 204 is removed (not shown). Solution is drawn from vial stopper 210 for injection (not shown). Blunt tip vial 206 is removed from the filled syringe using sheath 204 as a tool for removal. Safety apparatus 40 is attached with sheath 204 to a syringe 212 filled with solution to be injected, as shown in FIG. 24. Sheath 204 is removed. This positions extensible frame 56 in the ready to use position. An injection is performed. After reaching a predetermined depth, the face of safety tip cover 76 is forced rearward releasing locking pin 55 from uni-directional retaining pockets 66. Extensible frame 56 is in the retracted position. As needle 44 is removed from an injection site, extensible frame 56 travels with safety tip cover 76 to shield needle 44 and enclose distal end 48. After complete extraction, safety tip cover 76 extends slightly past distal end 48 positioning extensible frame 56 in the extended position such that safety apparatus 40 is in a disabled and locked condition.

Figure 25:
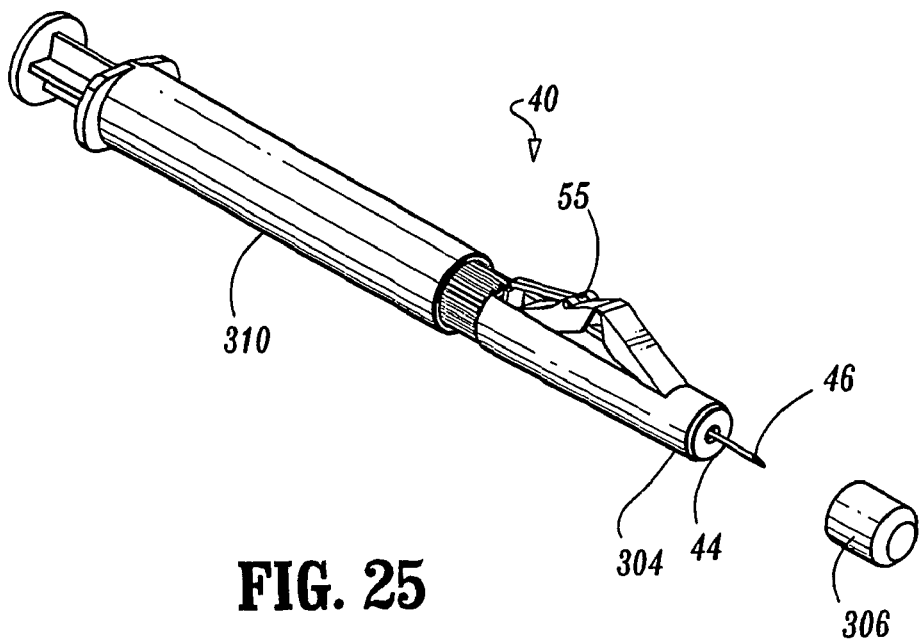
FIGS. 25 and 26 are perspective views illustrating operation of the safety apparatus shown in FIG. 16.
Figure 26:
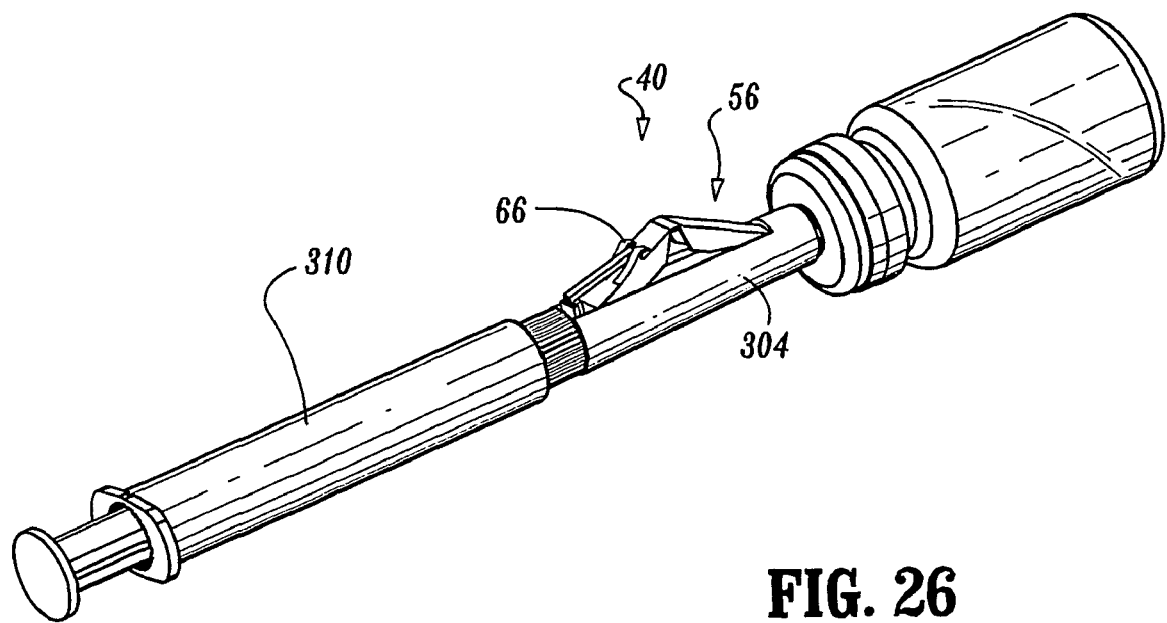

In another alternate embodiment, as shown in FIGS. 25 and 26, operation of safety apparatus 40, similar to those described, employs sheath 304 and is contemplated for use with a single needle to perform vial access and injection. Safety apparatus 40, with sheath 304, is attached to a syringe 310. Sheath cap 306 is removed to expose an adequate length of needle 44 to perform vial access. Needle 44 is inserted into a rubber vial stopper (not shown) and solution is drawn therefrom. Sheath 304 prevents the automatic locking features of safety apparatus 40, as discussed, from actuating. Sheath 304 is removed. This positions safety apparatus 40 in the ready to use position. An injection is performed. After reaching a predetermined depth, the face of the safety tip cover 76 is forced rearward releasing locking pin 55 from uni-directional retaining pockets 66. Extensible frame 56 is in the retracted position. As needle 44 is removed from the injection site, extensible frame 56 travels with safety tip cover 76 to shield needle 44 and enclose distal end 48. After complete extraction safety tip cover 76 extends slightly past distal end 48 positioning extensible frame 56 in the extended position such that safety apparatus 40 is in a disabled and locked condition.

Referring to FIGS. 27-30, in an alternate embodiment, a safety apparatus 440, similar to safety apparatus 40 described above, is shown. Safety apparatus 440 includes a needle hub 442 configured to support a medical needle cannula 444 having a sharpened distal end 446. Needle cannula 444 is supported by needle hub 442 at a proximal end 448 thereof and defines a longitudinal axis x. Needle hub 442 has a luer connection 443 for attachment with a syringe (not shown).

An extensible frame 456, includes a proximal segment 458 which is hingedly connected, via tab 459, to a distal segment 460. Proximal segment 458 is mounted to needle hub 442 via a pin hinge 462.

Figure 30:
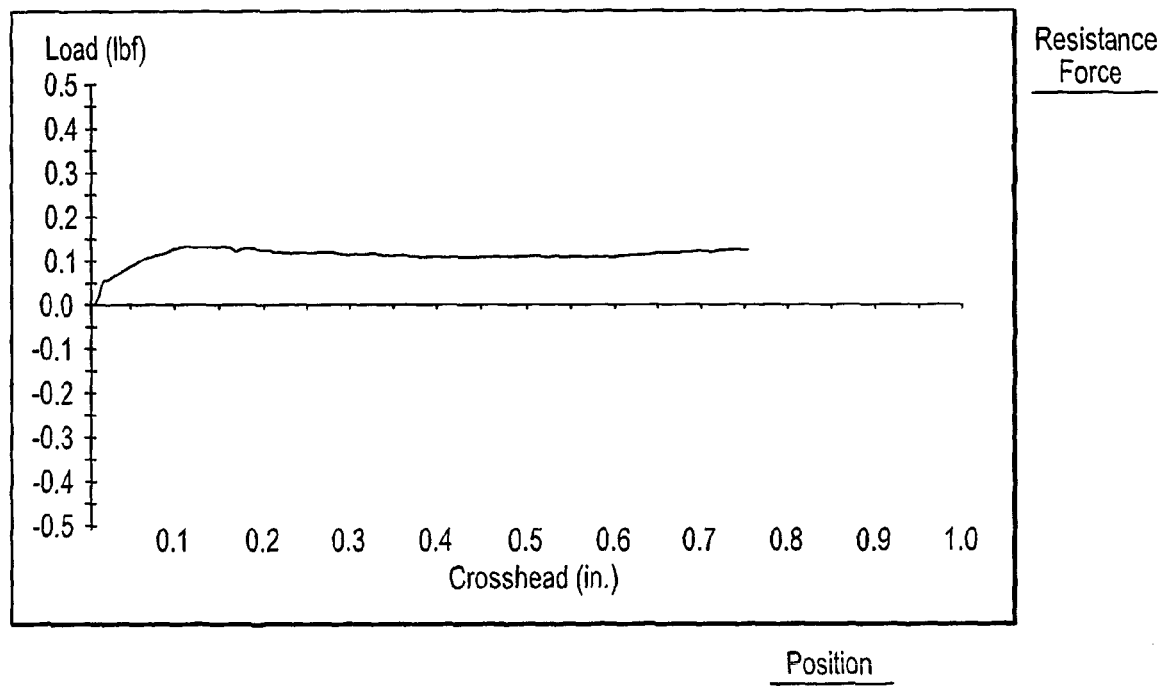
FIG. 30 is a graphical representation of resistance force versus safety tip cover position of the safety apparatus shown in FIG. 27.
Figure 28:
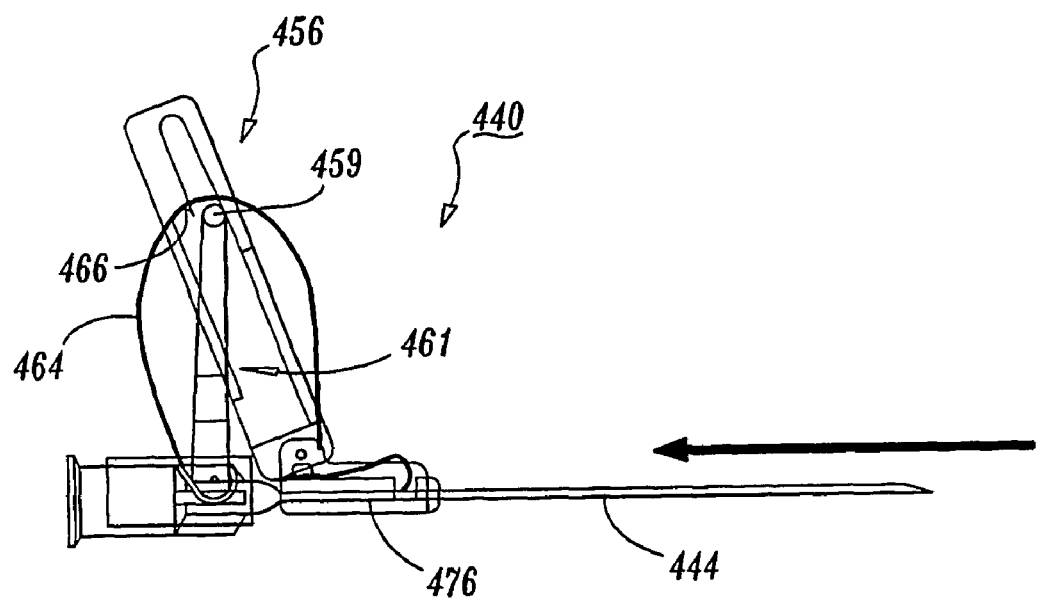
FIG. 28 is a side view of the safety apparatus shown in FIG. 27, in the retracted position.
Figure 29:
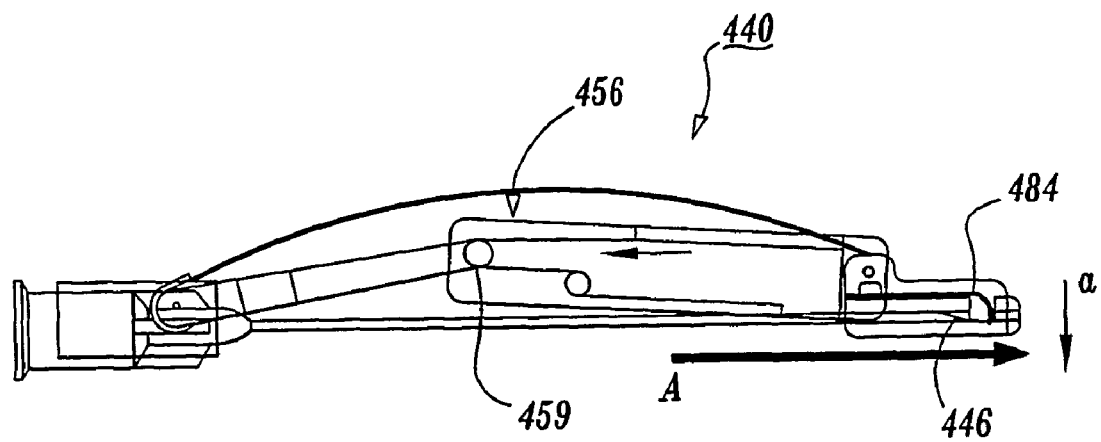
FIG. 29 is a side view of the safety apparatus shown in FIG. 27, in the extended position.

A resilient member, such as, for example, leaf spring 464 is coupled to proximal segment 458 and distal segment 460. Leaf spring 464 is configured to bias extensible frame 456 from a retracted position (FIG. 28) to an extended position (FIG. 29). The spring force applied from leaf spring 464 to extensible frame 456 is relatively constant. As shown in FIG. 30, which graphically illustrates resistance force versus safety tip cover position, this design results in a nearly constant resistive force as a function of extensible frame 456 position. Safety apparatus 440 has a safety tip cover 476, similar to safety tip cover 76 described above, for substantially enclosing distal end 446 of needle 444. Safety tip cover 476 employs a trap 484, similar to trap 84 described above, which biases to lock distal end 446 within safety tip cover 476.

Figure 27:
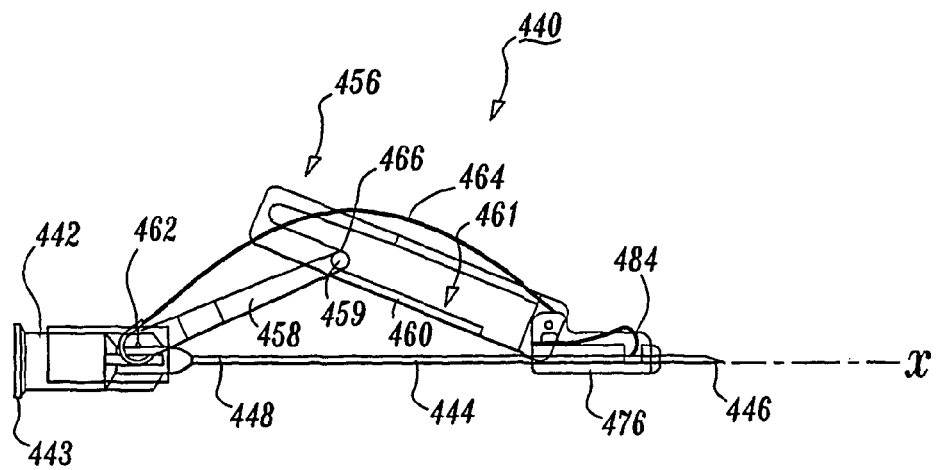
FIG. 27 is a side view of an alternate embodiment of the safety apparatus, in accordance with the principles of the present disclosure.

Proximal segment 458 includes tab 459 disposed for movement within a slot 461 of distal segment 460 to guide travel of extensible frame 456. Slot 461 includes a channel 466. Tab 459 is disposed in channel 466 to releasably fix extensible frame 456 between the retracted position and the extended position, in for example, a ready to use position (FIG. 27). The safety features of safety apparatus 440 are automatically deployed during a medical procedure, similar to those described above to prevent hazardous exposure to needle 444. It is contemplated that the tab and slot features may be alternatively disposed with the proximal segment, distal segment or any intermediate segment employed therewith.

Alternatively, the safety features may be manually activated by pressing on the top of extensible frame 456. This capability provides a backup in the event needle 444 is not inserted a sufficient depth into a subject to automatically deploy safety tip cover 476.

Prior to use of safety apparatus 440, extensible frame 456 is configured so that tab 459 is disposed in channel 466 of slot 461. This configuration restricts extension of extensible frame 456 to a ready to use position and locates safety tip cover 476 back slightly to reveal distal end 446 of needle 444. As shown in FIG. 28, when needle 444 is inserted, the subject's skin pushes safety tip cover 476 up the shaft of needle 444, in the direction of the arrow shown. As extensible frame 456 is rotated and compressed, tab 459 is pushed out of channel 466. Tab 459 is forced toward the upper portion of slot 461 subsequent to dislocation from channel 466 due to the spring force of leaf spring 464.

Safety tip cover 476 slides down the shaft of needle 444 as needle 444 is withdrawn from the subject, driven by the spring force of leaf spring 464. As shown in FIG. 29, extensible frame 456 expands to the extended position, in the direction of arrow A shown, as tab 459 is free to slide along slot 461. Trap 484 captures distal end 446, in the direction of arrow a shown, to prevent hazardous exposure thereto and such that safety apparatus 440 is in a locked and needle safe position.

Figure 31:
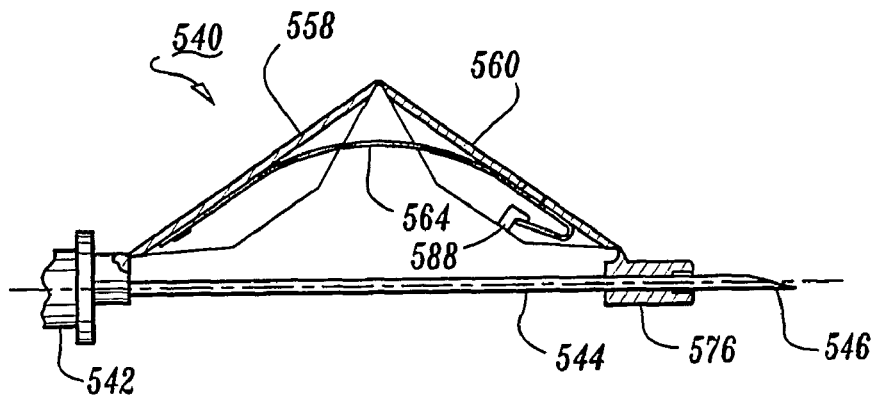
FIG. 31 is a side view of an alternate embodiment of the safety apparatus shown in FIG. 27.
Figure 32:
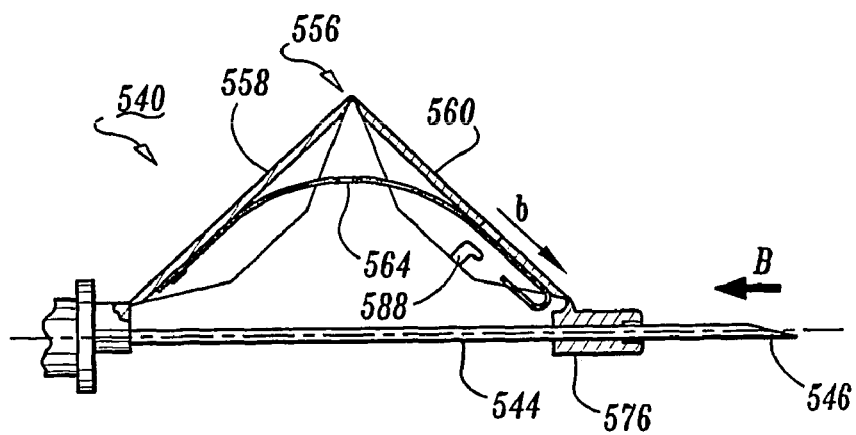
FIG. 32 is a side view of the safety apparatus shown in FIG. 31, in the retracted position.
Figure 33:
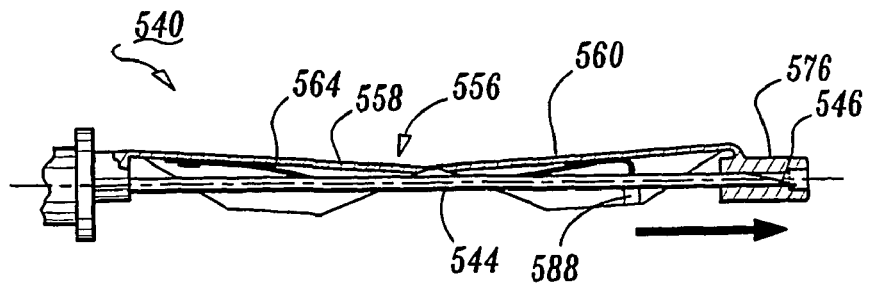
FIG. 33 is a side view of the safety apparatus shown in FIG. 31, in the extended position.

Referring to FIGS. 31-33, in an alternate embodiment, a safety apparatus 540, similar to those described above, is shown. Safety apparatus 540 includes a needle hub 542 configured to support a medical needle cannula 544 having a sharpened distal end 546. An extensible frame 556, includes a proximal segment 558 which is hingedly connected to a distal segment 560. Proximal segment 558 is mounted to needle hub 542. A leaf spring 564 is coupled to proximal segment 558 and distal segment 560. Leaf spring 564 is configured to bias extensible frame 556 from a retracted position (FIG. 31) to an extended position (FIG. 32). Safety apparatus 540 has a safety tip cover 576 for substantially enclosing distal end 546 of needle 544.

Leaf spring 564 is coupled to distal segment 560 via a catch 588 such that engagement of leaf spring 564 with catch 588 releasably fixes extensible frame 556 between the retracted position and the extended position, in for example, a ready to use position (FIG. 30). Prior to use of safety apparatus 540, extensible frame 556 is configured so that leaf spring 564 is releasably engaged with catch 588. This configuration restricts extension of extensible frame 556 to a ready to use position and locates safety tip cover 576 back slightly to reveal distal end 546 of needle 544. As shown in FIG. 31, when needle 544 is inserted into a subject, safety tip cover 576 is pushed up the shaft of needle 544, in the direction of arrow B shown. Leaf spring 564 is disengaged from catch 588, in the direction of arrow b shown. It is contemplated that catch 588 may be alternatively disposed with the proximal segment, distal segment or any intermediate segment employed therewith.

Safety tip cover 576 slides down the shaft of needle 544 as needle 544 is withdrawn from the subject, driven by the spring force of leaf spring 564. As shown in FIG. 32, extensible frame 556 expands to the extended position, in the direction of the arrow shown. Distal end 546 is captured by safety tip cover 576 due to over travel or in a manner consistent with the present disclosure. It is envisioned that extensible frame 556 may be locked in the extended position via manual pressure applied to force a lockout of extensible frame 556. It is further envisioned that extensible frame 556 may be locked, similar to that described herein.

It will be understood that various modifications may be made to the embodiments disclosed herein. Therefore, the above description should not be construed as limiting, but merely as exemplification of preferred embodiments. Those skilled in the art will envision other modifications within the scope and spirit of the claims appended hereto.

What is claimed is:

1. A safety apparatus comprising:
   a needle hub;
   an extensible frame connected to the needle hub, the extensible frame including a proximal segment and a distal segment, the extensible frame being resiliently biased from a retracted position to an extended position; and
   an arm member extending from any one of the needle hub and segments;
   wherein the arm member is configured to releasably engage any other one of the needle hub and segments to fix the extensible frame in a position between the retracted position and the extended position; and
   wherein engagement of the distal segment of the extensible frame with a subject during use moves the extensible frame towards the retracted position and releases the arm member from engagement with the one of the needle hub and segments.

2. A safety apparatus as recited in claim 1, wherein the arm extends from the needle hub.

3. A safety apparatus as recited in claim 1, wherein a resilient member is coupled to the needle hub and at least one segment, the resilient member being configured to bias the extensible frame from a retracted position to an extended position.

4. A safety apparatus as recited in claim 1, wherein a needle cover is connected to the distal segment.

5. A safety apparatus comprising:
   a needle hub having an arm extending therefrom; and
   an extensible frame connected to the needle hub, the extensible frame including a proximal segment and a distal segment, the extensible frame being resiliently biased from a retracted position to an extended position,
   wherein the arm is configured to releasably engage the proximal segment to fix the extensible frame in a position between the retracted position and the extended position.

6. A safety apparatus as recited in claim 5, wherein the extensible frame is resiliently biased via a coil spring disposed about a needle, said coil spring in an axial orientation with the needle and engaging the distal segment.

7. A safety apparatus as recited in claim 5, wherein a needle cover is coupled to the distal segment.

8. A safety apparatus as recited in claim 7, wherein the needle cover includes a biasing clip configured to substantially enclose a distal end of a needle.

9. A safety apparatus as recited in claim 7, wherein the needle cover defines a transverse cavity configured for receipt of a pin, the pin being slidable within the cavity to prevent distal movement of a needle disposed within the needle cover.

10. A safety apparatus as recited in claim 5, wherein one of the segments includes a catch tab configured to engage a needle such that the extensible frame is fixed in the extended position.

11. A safety apparatus as recited in claim 5, wherein one of the segments defines at least one retaining pocket and the arm has a locking pin disposed adjacent a distal end thereof, the locking pin being releasably engageable with the retaining pocket.

12. A safety apparatus as recited in claim 11, wherein the segment defines at least one retaining pocket, the retaining pocket having a flap preventing re-entry of the locking pin.

13. A method for infusing fluids to a subject, the method comprising:
   providing a safety apparatus including:
      a needle hub having an arm extending therefrom and configured to support a needle cannula,
      an extensible frame including a proximal segment being hingedly connected to a distal segment, the extensible frame being resiliently biased from a retracted position to an extended position,
      wherein the arm is configured to releasably engage the proximal segment to fix the extensible frame in a position between the retracted position and the extended position,
      a needle cover extending from the distal segment and being configured to substantially enclose a distal end of the needle cannula,
      and a sheath having a sheath cap and being configured to support the safety apparatus;
   attaching the needle hub to a syringe;
      removing the sheath cap to expose the needle cannula;
      drawing liquid via the needle cannula into the syringe;
      removing the sheath from the safety apparatus;
      performing an infusion with the syringe and safety apparatus;
      removing the needle cannula from the subject such that the needle cover automatically encloses the distal end of the needle cannula.

14. A method according to claim 13, wherein engagement of the distal segment of the extensible frame with the subject during use moves the extensible frame towards the retracted position and releases the arm member from engagement with the proximal segment.

15. A method for infusing fluids to a subject with a single needle, the method comprising:
   providing a safety apparatus including:
      a needle hub configured to support a needle cannula,
      an extensible frame, connected to the needle hub, including at least one segment and being resiliently biased from a retracted position to an extended position to actuate an automatic locking cover extending from the segment, and
      a sheath having a sheath cap and being configured to support the safety apparatus;
   attaching the needle hub to a syringe;
   removing the sheath cap to expose a length of the needle cannula;
   inserting the needle cannula in a vial to draw liquid, via the needle cannula, into the syringe such that the sheath prevents the automatic locking cover from actuating;
   removing the sheath from the safety apparatus without actuating the automatic locking cover;
   performing an infusion with the syringe and safety apparatus;
   removing the needle cannula from the subject such that the locking cover automatically encloses a distal end of the needle cannula.

16. A method for infusing fluids to a subject with a single needle, the method comprising:
   providing a safety apparatus including a needle cannula and a sheath having a sheath cap;
   removing the sheath cap to expose a length of the needle cannula;
   inserting the needle cannula in a vial to draw liquid, via the needle cannula, into a syringe;
   removing the sheath from the safety apparatus;
   performing an infusion with the syringe and safety apparatus; and
   removing the needle cannula from the subject.

* * * * *